(12) United States Patent
Rosenblatt et al.

(10) Patent No.: US 6,355,790 B1
(45) Date of Patent: Mar. 12, 2002

(54) INHIBITION OF HIV REPLICATION USING A MUTATED TRANSFER RNA PRIMER

(75) Inventors: Joseph D. Rosenblatt, Rochester, NY (US); Xinqiang Li, San Diego, CA (US)

(73) Assignees: University of Rochester, Rochester, NY (US); University of California, Oakland, CA (US)

( * ) Notice: Subject to any disclaimer, the term of this patent is extended or adjusted under 35 U.S.C. 154(b) by 0 days.

(21) Appl. No.: 08/866,116

(22) Filed: Jun. 3, 1997

(51) Int. Cl.$^7$ .................. C12N 15/11; C12N 15/85; C07H 21/04

(52) U.S. Cl. ................ 536/24.5; 536/23.1; 536/24.1; 435/325; 435/366; 435/372.3; 435/375

(58) Field of Search .................. 435/6, 440, 184, 435/325, 366, 372.3, 375, 320.1; 536/23.1, 24.1, 24.31, 24.33, 24.5; 514/44

(56) References Cited

PUBLICATIONS

Huang, Y. et al. J. of Virology, Dec. 1994. pp. 7676–7683. vol. 68. No. 12.*
Anderson, W.F. Human Gene Therapy. Nature. vol. 392. Supp. Apr. 30, 1998. pp. 25–30.*
Wohrl, B.M. et al. J. of Biological Chemistry. vol. 268. No. 18. Jun. 25, 1993. pp. 13617–13624.*
Gobbers, E. et al. J. of Virological Methods. vol. 66. (1997). pp. 293–301.*
Roy et al., "Nucleotide Sequence of a Segment of Human DNA Containing the Three tRNA Genes," *Nuc. Acids Res.*, 10(22):7313–7322 (1982).
Chatterjee et al., "Dual–Target Inhibition of HIV–1 in Vitro by Means of an Adeno–Associated Virus Antisense Vector," *Science*, 258:1485–1488 (1992).
Tuerk et al., "RNA Pseudoknots that Inhibit Human Immunodeficiency Virus Type 1 Reverse Transcriptase," *Proc. Natl. Acad. Sci. U.S.A.*, 89:6988–6992 (1992).

Essink et al., "Structural Requirements for the Binding of tRNA$_3^{Lys}$ to Reverse Transcriptase of the Human Immunodeficiency Virus Type 1," *J. Biol. Chem.*, 270(40):23867–23874 (1995).
Wakefield et al., "Construction of a Type 1 Human Immunodeficiency Virus that Maintains a Primer Binding Site Complementary to tRNA$^{His}$," *J. Virol.*, 70(2):966–975 (1996).
Biasolo et al., "A New Antisense tRNA Construct for the Genetic Treatment of Human Immunodeficiency Virus Type 1 Infection," *J. Virol.*, 70(4):2154–2161 (1996).
Harrich et al., "A Critical Role for the TAR Element in Promoting Efficient Human Immunodeficiency Virus Type 1 Reverse Transcription," *J. Virol.*, 70(6):4017–4027 (1996).
Lu et al., "Inhibiton of HIV–1 Replication Using a Mutated tRNA$^{Lys-3}$ Primer," *J. Biol. Chem.*, 272(23):14523–14531 (1997).
Ben–Artzi et al., "Double–Stranded RNA–Dependent RNase Activity Associated with Human Immunodeficiency Virus Type 1 Reverse Transcriptase," *Proc. Natl. Acad. Sci. USA*, 89:927–931 (1992).
Good, et al., "Expression of Small, Therapeutic RNAs in Human Cell Nuclei," *Gene Ther*, 4(1):45–54 (1997) (abstract only).

* cited by examiner

*Primary Examiner*—Sean McGarry
*Assistant Examiner*—Mark L. Shibuya
(74) *Attorney, Agent, or Firm*—Nixon Peabody LLP

(57) ABSTRACT

Modified tRNA molecules are provided which inhibit HIV-1 replication. A tRNA molecule has a modified aminoacyl acceptor stem with a 3' segment which has reduced complementarity to the HIV primer binding site can initiate aberrant reverse transcription and/or interfere with reverse transcription. tRNA molecules which are modified in regions outside the acceptor stem which interact with reverse trancriptase or the HIV-1 RNA template can also inhibit HIV-1 replication. Methods are disclosed for introducing the modified tRNA molecules into human cells.

17 Claims, 12 Drawing Sheets

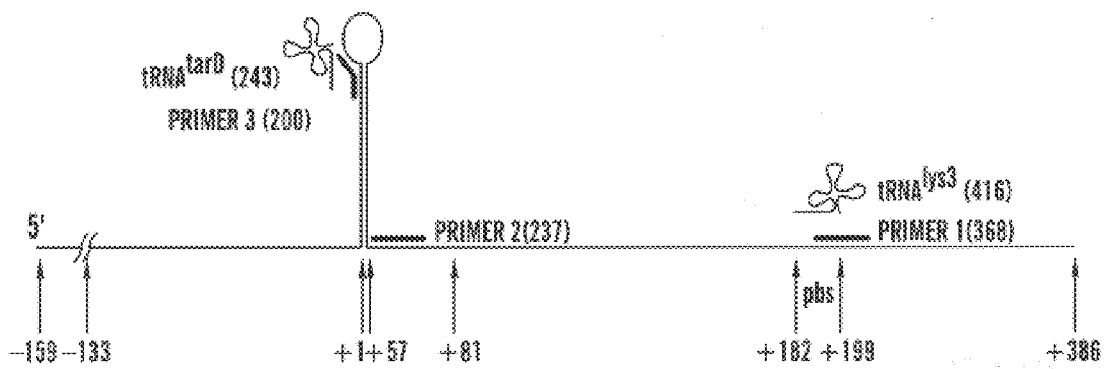
FIG. 8A
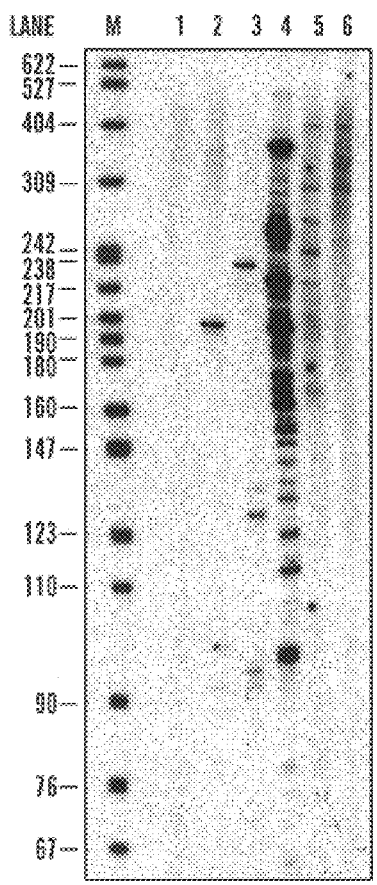 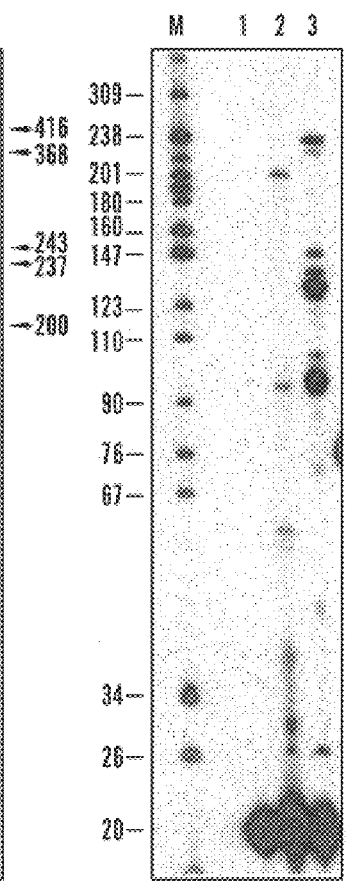 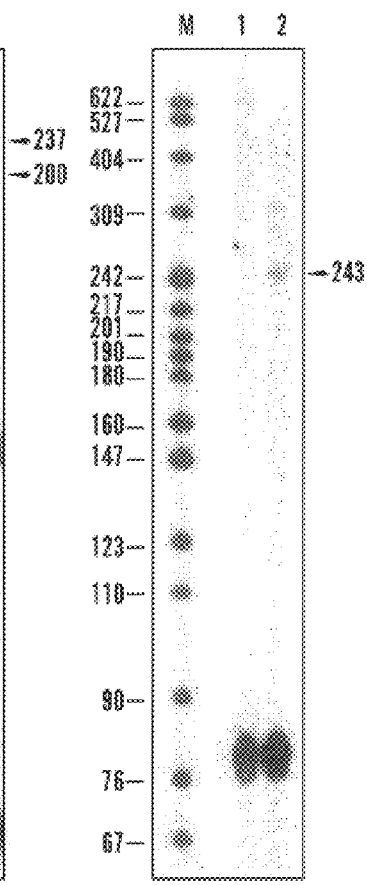
FIG. 8B    FIG. 8C    FIG. 8D

INHIBITION OF HIV REPLICATION USING A MUTATED TRANSFER RNA PRIMER

The subject matter of this application was made with support from the United States Government under Grant No. R01 A13655 from the National Institutes of Health and MH-199200 from the National Institute for Mental Health. The United States Government may have certain rights.

FIELD OF THE INVENTION

The present invention relates to a modified tRNA molecule which inhibits the full length reverse transcription of HIV-1 and HIV-1 replication. The invention further relates to a method for inhibiting the replication of HIV-1 in human cells.

BACKGROUND OF THE INVENTION

A retrovirus designated human immuno-deficiency virus ("HIV") is the causative agent of the complex disease termed Acquired Immune Deficiency Syndrome ("AIDS") and is a member of the lentivirus family of retroviruses. M. A. Gonda, et al., *Science* 227, 173, (1985); P. Sonigo, et al., *Cell* 42, 369, (1985). The complex disease AIDS includes progressive destruction of the immune system and degeneration of the central and peripheral nervous systems. The HIV virus was previously known or referred to as LAV, HTLV-III, or ARV. The Centers for Disease Control ("CDC") reported the number of AIDS deaths for the first six months of 1996 was 22,000 nationwide.

tRNA functions in living cells mainly as a vehicle to translate genetic information stored in mRNA into amino acid sequence in proteins. Cellular tRNAs are recognized by many cellular proteins including 5' and 3' tRNA processing enzymes (Altman, S., *Cell* 23, 1–5 (1981)) and tRNA aminoacyl transferases (aa-tRNA synthetase) (Sampson, J. R., et al.,*Biochemistry* 29, 2523–2532 (1990); Behlen, L. S., et al., *Biochemistry* 29, 2515–2523 (1990)). Most of these enzymes recognize both the anticodon region and specific features of the tridimensional structure of tRNA (Sampson, J. R., et al., *Biochemistry* 29, 2523–2532 (1990)). There are two different human tRNA$^{Lys}$ genes. One of these, tRNAlys-UUU (Roy, K. L., et al., *Nuc. Acids Res.* 10, 7313–7322 (1982); Richter-Cook, N. J., et al., *J. Biol. Chem.* 267, 15952–15957 (1992)), has a complementary sequence to the HIV-1 RNA genome in the region of the prime binding sequence (PBS), and is used as the primer for HIV-1 reverse transcription.

Human immunodeficiency virus type-1 ("HIV-1") relies on multiple human cellular factors for its own replication (Steffy, K., et al., *Microbiol Rev* 55(2), 193–205 (1991)). In particular, tRNA$^{Lys3}$ is utilized by HIV-1 at the earliest step of its life cycle (Weiss, S., et al., *Gene* 111(2), 183–97 (1992), Das, A. T., et al., *FEBS Lett.* 341, 49–53 (1994); Arts, E., et al., *J. Biol. Chem.* 269, 14672–14680 (1994); Barat, C., et al., *Embo J* 8(11), 3279–85 (1989); Barat, C., et al., *Nucleic Acids Res* 19(4), 751–7 (1991); Khan, R., et al.,*J Biol Chem* 267(10), 6689–95 (1992)). During the first step of reverse transcription, the single stranded plus-sense RNA genome is copied into minus-sense cDNA beginning at the 3' end of a partially annealed tRNA$^{Lys3}$ primer (Peliska, J. A., et al., *Science* 258, 1112–1118 (1992)). Several reports indicated that p66 of the HIV-1 RT p51/p66 heterodimer recognizes and binds to the tRNA$^{Lys3}$ anticodon region (DeVico, A. L., et al.,*J. Biol. Chem.* 266, 6774–6779 (1991); Sarih-Cottin, L., et al.,*J Mol Biol* 226(1), 1–6 (1992); Rhim, H., et al., *J Virol* 65(9), 4555–64 (1991); Kohlstaedt, L. A., et al., *Proc. Natl. Acad. Sci. USA* 89, 9652–9656 (1992)) and may help unwind the acceptor stem (Kohlstaedt, L. A., et al., *Proc. Natl. Acad. Sci. USA* 89, 9652–9656 (1992)) in the presence of NCp7 protein (Barat, C., et al., *Nucleic Acids Res* 19(4), 751–7 (1991)). Another report demonstrated that excess wild type tRNA$^{Lys3}$ primer inhibited the DNA polymerase activity of a recombinant HIV-1 RT, p66/p51 heterodimeric form (Bordier, B., et al., *Nucleic Acids Res* 18(3), 429–36 (1990)). This effect was ascribed to the anticodon region of tRNA$^{Lys3}$ primer (Bordier, B., et al., *Nucleic Acids Res* 18(3), 429–36 (1990)). The necessary role for tRNA$^{Lys3}$ in HIV-1 reverse transcription, its specific affinity for HIV-1 RT, and its association with HIV-1 virions suggests that mutated derivatives of the tRNA$^{Lys3}$ primer might interfere with the viral replication cycle.

HIV-1 specific ribozymes, antisense RNA, and RNA decoys have been proposed as potential therapeutic reagents for HIV-1 (Chatterjee, S., et al., *Science* 258, 1485–1488 (1992); Sullenger, B. A., et al., *Cell* 63, 601–608 (1990); Ojwang, J. O., et al., *PNAS* 89, 10802–10806 (1992)).

Presently, a triple-drug therapy regimen is the most effective approach to controlling the AIDS virus. The cocktail therapy consists of a combination of a protease inhibitor called indinavir with two reverse-transcriptase inhibitors known as AZT and 3TC. The triple drug therapy results in a decrease in measured levels of virus in both blood and lymphatic tissues. However, a proportion of those treated, whose viruses had developed resistance to one or more of the cocktail's reverse-transcriptase inhibitors as a result of previous treatment, fail to respond. Some studies have projected that combination therapy can virtually eliminate the AIDS virus from those patients who respond within two or three years. However, other studies indicate that minimal residual virus is sufficient to cause relapse. In addition, existing pharmacologic therapies leave residual HIV genes lurking in cells in the form of latent "provirus." As long as the cells remain alive, these genes can be transcribed, rekindling virus production. Therefore, drug therapy may need to be maintained throughout the patient's life. The therapy may have long term adverse side effects and treatments can cost over $15,000 annually for each patient. Thus, there is a continuing need to develop additional approaches to controlling HIV infection which can be used alone or in combination with existing therapies.

SUMMARY OF THE INVENTION

One aspect of the present invention relates to a modified tRNA$^{Lys3}$ molecule for inhibiting HIV template replication. The tRNA molecule has an acceptor stem having 3' and 5' segments which form a secondary structure. Furthermore, the 3' segment hag a nucleic acid sequence with reduced complementarity to the HIV-1 primer binding site compared to the 3' segment of a wild type tRNA$^{Lys3}$. The 5' segment has sufficient homology with the 3' segment to maintain the secondary structure of the acceptor stem.

Another aspect of the present invention relates to a tRNA$^{Lys3}$ molecule which is modified to inhibit the interaction of the tRNA$^{Lys3}$ molecule with HIV-1 reverse transcriptase or HIV-1 RNA template. In this aspect of the invention, the tRNA$^{Lys3}$ molecule is modified in a region other than its acceptor stem.

The present invention also provides a method of inhibiting HIV infectivity in human cells by introducing the modified tRNA$^{Lys3}$ molecules of the invention into human cells.

BRIEF DESCRIPTION OF THE DRAWINGS

FIGS. 3 A–B show the presence of tRNA$^{Lys3}$ and tRNA$^{tarD}$ in cells transduced with retroviral vectors.

FIGS. 4 A–C show the decreased susceptibility of uncloned, tRNA$^{tarD}$-transduced cells to HIV-1. Decreased susceptibility of uncloned, tRNAtarD-transduced cells to HIV-1. MT-2 Cells were transduced with the retroviral vectors LN (MT-2/LN) or N2A-tarD (MT-2/TAR-D) and selected with G-418 as described in the Examples; transduced cultures were infected with HIV-1 prior to cell subcloning.

FIGS. 5 A–B demonstrate the decreased susceptibility of individual clones of tRNA$^{tarD}$-transduced cells to HIV-1.

FIG. 8 A–D depict the effect of tRNAtarD on the initiation of reverse transcription by HIV-1 RT. FIG. 8A is a schematic representation of substrates used in the reaction. RNA 1, RNA 2, DNA primers 1, 2 and 3, tRNA$^{Lys3}$ and tRNAtarD were prepared as described in the Examples. RNA and DNA are represented by thin and thick lines, respectively. The maximum length minus strand DNA extension products made by the action of HIV-1 RT on different primers are marked against each substrate within parenthesis. The nucleotide positions corresponding to the HIV-1 genome are numbered above the RNA template. The 3' end of RNA 2 is at position +81 such that it lacks the PBS. FIG. 8B identifies the reaction products of reverse transcription from different primers on template RNA 1. Conditions for RNA dependent DNA polymerase assays are as described in the Examples. Extension products were monitored by the incorporation of P$^{32}$-labeled dCTP. Lane M shows DNA molecular weight markers comprised of fragments derived from Msp I-digested pBR322. Reaction products from DNA primers 3, 2, and 1 and primers tRNA$^{Lys3}$, tRNAtarD, are in lanes 2 through 5, respectively. Lane 1 does not contain any primer. FIG. 8C shows the reaction products of reverse transcription from different DNA polymerase assays as described in the Examples. 5'-end labeled DNA primers were employed and unlabeled dNTPs were used in the extension reactions. Lane M shows DNA molecular weight markers. Reaction products from primers DNA primers 1, 3, and 2 are in lanes 1 through 3, reopectively. FIG. 8D shows the reaction products of reverse transcription from primers tRNA$^{Lys3}$ and tRNAtarD on template RNA 2. P$^{32}$-labeled tRNA$^{Lys3}$ or tRNAtarD primers were used and extension reactions carried out as above. Reaction products from primers tRNA$^{Lys3}$ and tRNAtarD are in lanes 1 and 2, respectively.

DETAILED DESCRIPTION OF THE INVENTION

Figure 1A:
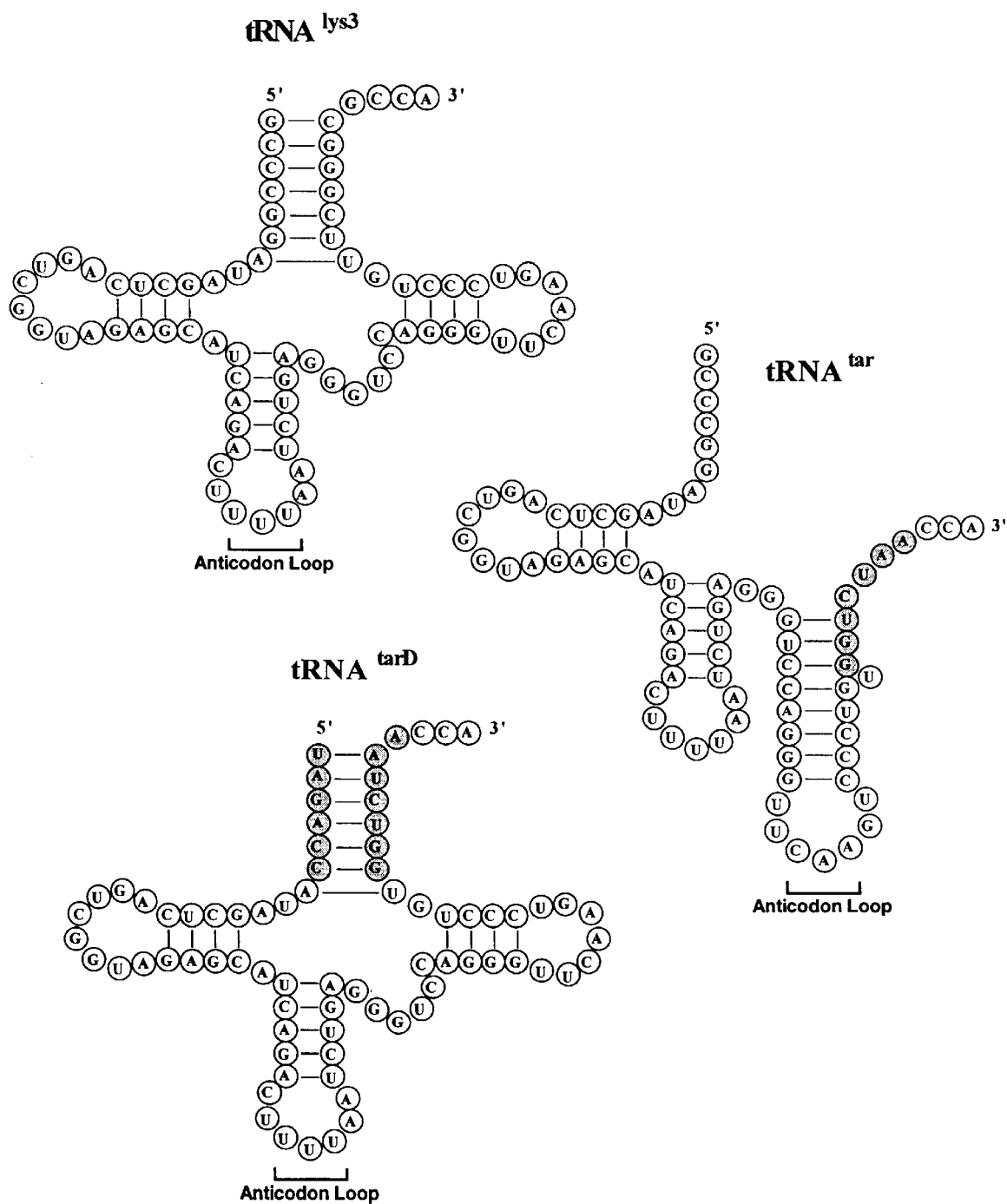
FIG. 1A shows the sequences and secondary structures of tRNA$^{Lys3}$ (SEQ ID No: 19), tRNA$^{tar}$ (SEQ ID No: 20), and tRNA$^{tarD}$ (SEQ ID No: 2). tRNA$^{Lys3}$, tRNA$^{tar}$, and tRNA$^{tarD}$ are presented in secondary structures generated by the program "RNA fold". The filled circles represent mutated nucleotides in tRNA$^{tar}$, and tRNA$^{tarD}$.

Important parameters to ensure the efficacy of anti-viral molecules against HIV-1 infection are high levels of intracellular expression, efficient association with HIV-1 RNA, and decreased risk for development of resistant viral strains. A gene was constructed encoding a tRNA$^{Lys3}$-derived mutant in which both the 3' primer-binding region and corresponding 5' complementary sequences were altered, but which theoretically retains natural secondary and tertiary tRNA structure (Sampson, J. R., et al., Biochemistry 29, 2523–2532 (1990); Behlen, L. S., et al., Biochemistry 29, 2515–2523 (1990), which are hereby incorporated by reference). The mutant tRNA has 3' sequences complementary to the highly conserved TAR region of HIV-1. Mutant tRNA is able to interact specifically with purified HIV-1 RT and can serve as a primer for reverse transcriptase in vitro. Furthermore, constitutive expression of tRNA$^{tarD}$ in T-cell lines following retroviral transduction results in decreased HIV-1 replication, as assayed by p24 levels, or by relative TCID$_{50}$ titer in the MT-2 and CEM T-cell lines.

One aspect of the present invention provides a modified tRNA$^{Lys3}$ molecule for inhibiting replication of an HIV-1 template having a primer binding site. The modified tRNA molecule has an acceptor stem having 3' and 5' segments where the 3' and 5' segments form a secondary structure. The 3' segment has a nucleic acid sequence with reduced complementarity to the primer binding site of the HIV-1 template compared to the 3' segment of a wild-type tRNA$^{Lys3}$ molecule. The 5' segment has sufficient homology with the 3' segment to maintain the secondary structure of the acceptor stem.

The 3' segment may be modified to have complementarity to a region of the HIV-1 template outside of the primer binding site. This type of modified tRNA$^{Lys3}$ molecule can also promote aberrant transcription initiation. Residual affinity for the primer binding site may exist. Alternatively, the 3' region may not have complementarity to any region of the HIV-1 template.

In a preferred embodiment of the invention, the tRNA molecule has the conserved A and B boxes of tRNA$^{Lys3}$. The so-called "A" and "B" boxes are needed for polymerase III-directed transcription (Geiduschek, E. P., et al., *Ann. Rev. Biochem.* 57, 873–914 (1988), which is hereby incorporated by reference).

The modified tRNA molecule may have the anticodon region of tRNA$^{Lys3}$. Moreover, the nucleic acid sequence of the anticodon loop may be further mutated to inhibit HIV replication. Such mutant tRNAs may have interesting properties. The anticodon loop USUU motif is thought to interact with the AAAA motif (nucleotides 169–172) located within the postulated U5-IR loop in HIV-1 (Isel, et al., *J. Mol. Biol.* 247, 236–50 (1995); Isel, et al., *J. Biol. Chem.* 268, 25269–72 (1993), which are hereby incorporated by reference). Mutations within the anticodon loop will need to be carefully evaluated for changes in affinity to the HIV-1 RT. In addition such alterations may interfere with intermolecular base pairing between tRNA$^{Lys3}$ and the AAAA motif, potentially decreasing targeting to the PBS or altering the positioning of tRNA on the template (Arts, et al., *J. Biol. Chem.* 269, 14672–80 (1994); Wakefield, et al., *J. Virol.* 68, 1605–14 (1994), which are hereby incorporated by reference). The invention therefore provides a modified tRNA molecule where the nucleic acid sequence of the anticodon loop is mutated within a USUU motif of the anticodon loop to inhibit HIV-1 replication.

The modified tRNA molecule may also have a 3' terminal sequence of 5'-CCA-3'. The 3' terminal CCA is homologous to a portion of the primer binding site in the HIV template and plays a role in transcription initiation The terminal trinucleotide CCA is added post-transcriptionally to all tRNAs by the enzyme ATP/CTP;tRNA nucleotidyl transferase and is not encoded in unmodified tRNA genes (Spacciapoli, et al., *J. Mol. Recognit.* 3, 149–55 (1990), which is hereby incorporated by reference). Mutants within the acceptor stem may not be post-transcriptionally modified in a normal fashion and may, therefore, lack the terminal CCA. If this is the case, priming will not be able to initiate from the normal CCA homology within the PBS. Synthetic genes encoding modified tRNAs could be constructed with the terminal CAA in place. Alternative variants may be specifically designed to lack the terminal CCA.

Mutant tRNAs, including those lacking the terminal CCA, which are incapable of or deficient in ability to be aminoacylated, may be incorporated more efficiently into viruses and/or may be more readily used as primers by the HIV-1 reverse transcriptase.

The modified tRNA molecule may also have the TΨC loop of tRNA$^{Lys3}$. As above the nucleic acid sequence of the TΨC loop may be mutated to decrease HIV particle formation. The TΨC loop may be important in RT recognition and, also, in direct interaction with sequences adjacent to the primer binding site ("PBS"). This type of mutant may have interesting properties. Several different classes of mutants may be feasible, with different potential phenotypes. First, it is unclear whether mutant tRNA will be appropriately modified to generate the modified bases within the TΨC loop including A$^{ml}$ (residue 58), Ψ (residue 55), and Tm (residue 54). Mechanisms governing base modification have not been well characterized for mammalian tRNAs. Experiments in yeast tRNA$^{Phe}$ indicate that reverse transcription is slowed or stopped by the presence of the 1-methyl adenine modification, and this is thought to be the case for reverse transcription of tRNA$^{Lys3}$ as well (Wittig, et al., *Nucleic Acids Res.* 5, 1165–78 (1978), which is hereby incorporated by reference). If the A$^{ml}$ is not present, reverse transcriptase may not pause appropriately during plus strand synthesis, and may actually read into and beyond the TΨC loop sequences. This could disrupt base pairing between the minus strand and plus strand as well as extension of the plus strand due to lack of complementarity of the tRNA derived sequences with the plus strand template. Accordingly, a preferred embodiment of the invention is where the nucleic acid sequence of the TΨC loop is mutated at a position selected from the group consisting of position 58, position 55, and position 54.

Deliberate mutations can be introduced into the position 58 "A" residue in tRNA$^{Lys3}$ which cannot undergo modification to A$^{ml}$. Additional mutations may also be introduced into the position 54, and/or 55 to prevent modification to Tm or Ψ respectively.

Another mutant could introduce alterations into the $^{50}$AGGGTmΨ$^{55}$ (superscripted numbers indicate tRNA position) motif to decrease base pairing to the GACCCU (nucleotides 149–154) in HIV-1 proposed by Wakefield and colleagues (Wakefield, et al., *J. Virol.* 68, 1605–14 (1994), which is hereby incorporated by reference). The latter and other tRNA TΨC loop template interactions will need to be carefully evaluated for affinity to RT, as well as for effects on Pol III transcription, due to the known importance of "A" and "B" box sequences in pol III transcription. Another preferred embodiment of the invention is where the nucleic acid sequence of the TΨC loop is mutated in the $^{50}$AGGGTmΨ$^{55}$ motif.

The modified tRNA$^{Lys3}$ molecule may have a 3' segment with nucleic acid sequence complementary to a region of the HIV template other than the primer binding site. A preferred embodiment of the invention is where the modified tRNA molecule has a 3' segment with a nucleic acid sequence complementary to TAR. Mutants which are complementary to areas of the HIV-1 genome other than TAR with low potential homology to the PBS are also preferred. Those sites which may be suitable include U3, gag/pol, etc. Mutants with extended complementarity, i.e. longer than the 18 base PBS homology, may be used as well as mutants with limited complementarity.

A preferred embodiment of the modified tRNA molecule has a 3' segment with the nucleic acid sequence 5'-GGUCUAACCA-3' (SEQ ID NO: 1). A more preferred embodiment of the modified tRNA molecule has a 3' segment with the nucleic acid sequence 5'-UAGACC-3'. An even more preferred embodiment is where the modified tRNA molecule has the nucleic acid sequence as shown in SEQ ID NO: 2 as follows:

5'-UAGACCAUAGCUCAGUCGGUAGAGCAU-
CAGACUUUUAAUCUGAGGGUCCAGGGUU-
CAAGUCCCUGUGGUCUAACCA-3'.

Multiple strains and isolates of HIV have been identified. A preferred embodiment of the invention is where the HIV transcript is an HIV-1 transcript.

The invention further provides a gene encoding the modified tRNA molecule. A preferred embodiment of the invention is a gene encoding mutations introduced into tRNAlys-UUU (tRNA$^{Lys3}$) designed to alter PBS binding specificity, while maintaining conserved tRNA$^{Lys3}$ sequences in the so-called "A" and "B" boxes needed for polymerase III-directed transcription (Geiduschek, E. P., et al., *Ann. Rev. Biochem.* 57, 873–914 (1988), which is hereby incorporated by reference). In this embodiment, the integrity of the anticodon region is maintained. The modified tRNA$^{Lys3}$ may also have substituted sequences in the acceptor stem, to make a 3' domain complementary to the conserved HIV-1 TAR region.

Promoters of various genes, like those of 5S genes, contain internal control regions ("ICRs"). These ICRs have been located by resection approaches applied to Xenopus tRNA$^{Leu}$ (Galli et al., *Nature* 294:626–631 (1981)) and tRNA$^{Met}$- (Hofstetter et al., *Cell* 24:573–585 (1981)), *D. melanogaster* tRNA$^{Arg}$ (Sharp et al., *Proc. Natl. Acad. Sci. USA* 78:6657–6661 (1981)), *Caenorhabditis elegans* tRN$^{Pro}$ (Ciliberto et al., *Proc. Natl. Acad. Sci. USA* 79:1195–1199 (1982)), and *Bombyx mori* tRNA$^{Ala}$ genes (Larson et al., *Proc. Natl. Acad. Sci. USA* 80:3416–3420 (1983)). Internal deletions and substitutions in these genes define two domains, box A and box B, having approximate coordinates 8–19 and 52–62, respectively[2]. The discontinuous nature of the ICR is made apparent by a detailed analysis of point mutants in the coding region of the *S. cerevisiae* tRNA$^{Tyr}$ gene. Substitutions at 3 positions 5' to box A, at 13 positions between box A and box B, and at 5 positions 3' to box B have no effect on transcription (Koski et al., *Nucleic Acids Res.* 10:8127–8143 (1982); Baker et al., *Proc. Natl. Acad. Sci. USA* 84:8768–8772 (1987); Allison et al., *Cell* 34:655–664 (1983)). The two boxes contain nucleotides that are highly conserved in all tRNAs: the invariant $U_8$, $A_{14}$, $G_{18}$, and $G_{19}$ are in box A; $G_{53}$, $T_{55}$, $C_{56}$, $A_{58}$, and $C_{61}$ are in box B. A general consensus sequence for each box (Galli et al., *Nature* 294:626–631 (1981)) can be set down (Table 1). In natural yeast tRNA genes, distances between boxes A and B vary from 31 to 93 bp, due to the varying lengths of extra arms and the presence of intervening sequences within certain tRNA genes.

The analysis of mutations within the coding sequences of several tRNA genes and experiments to determine DNA contacts of the *S. cerevisiae* TFIIIC-like τ protein (Table 1 and see below) suggest that box B should be extended to bp 45 because of mutations in various genes at bp 45–49 as shown in Table 1, and because of protein-DNA contacts at bp 47–51. The extended is called the box "B+" (bp 45–62). The 5' extension of box B+ resembles the intermediate element of the 5S ICR. The fact that the 5' extensions of different tRNA genes in Table 1 are not aligned probably indicates that there is a short spacer sequence between each 5' extension and the core consensus sequence, and that the lengths of these spacers are not the same in different genes. The other aspects of Table 1 should also be noted. The existence of promoter-down mutants where the consensus sequence specifies N probably signifies that genes with varying levels of expression have been grouped together in deriving the consensus. The existence of neutral mutations where the consensus sequence specifies particular nucleotides probably signifies conservation relating to other functions in addition to promoter strength.

| Gene | Box A | Box B | Transcription system | References |
|---|---|---|---|---|
| | | - T | | |
| | +- + - - | ++ - - + | | |
| *S. cerevisiae* | GT G T A | AG A GC C | *S. cerevisise* | 105–108 |
| | x x | xxxx x | | |
| tRNA$^{Tyr}$ | TAGCCAAGTTGG | GATCGGGCGTTCGACTCG | | |
| | (SEQ. ID. No. 19) | (SEQ. ID. No. 20) | | |
| | | - | | |
| | - -- | T+ - -- - | | |
| *S. pombe* | T TA | AC A AG T | *S. cerevisiae* | M. Nichols, D. Söll, personal |
| | x | xx | | |
| tRNA$^{Ser}$ | TGTCCGAGT GG | CCGCGCAGGTTCAAATCC | | communication |
| | (SEQ. ID. No. 21) | (SEQ. ID. No. 22) | | |
| | | -- - ---- | | |
| *C. elegans* | | AA T ACAT | | |
| | | x | | |
| tRNA$^{Pro}$ | | GGTCCCGGGTTCAATCCC | HeLa | 81, 109 |
| | | (SEQ. ID. No. 23) | | |
| | -- | - - - | | |

-continued

| Gene | Mutations | | Transcription | |
| --- | --- | --- | --- | --- |
| | Box A | Box B | system | References |
| Xenopus | TA      A | A   T    T | Xenopus oocyte | |
| | x x | x            x | | |
| tRNA<sup>Met</sup> | TGGCGCAGC GG | GGTCGATGGATCGAAACC | (Injection) | 79, 110 |
| | (SEQ. ID. No. 24) | (SEQ. ID. No. 25) | | |
| CONSENSUS | TRGCNNAGY GG | GGTTCGANTCC | | |
| | \|      \| | \|      \| | | |
| | 10 | 60 | | |
| | (SEQ. ID. No. 25) | (SEQ. ID. No. 27) | | |
| Contacts with factor C/τ in the major groove | | | | |
| S. cerevisiae | ' *   * '' | *  ''' '*'  '* '  '''' * | S. cerevisiae | 111 |
| tRNA<sup>Glu</sup> | TAGTGTAAC GG | AGACCGGGGTTCGACTCCCCG | | |
| | (SEQ. ID. No. 28) | (SEQ. ID. No. 29) | | |
| S. cerevisiae | ''*'*  '*  '' | '*  '  '  ''' * * | S. cerevisiae | 112 |
| tRNA<sup>Leu</sup> | TGGCCGAGC GG | ATGCAAGAGTTCGAATCTCTT | | |
| | (SEQ. ID. No. 30) | (SEQ. ID. No. 31) | | |

This compilation has been made by B. D. Hall and is reproduced here with his generous permission. Sequences are written in the nontrancsribed strand. The letters above each time show changes that generate promoter-up (+) and down (-) effects. Base pairs at which promoter-neutral changes have been observed are designated by (x). The DNA contacts shown on the two bottom lines are deduced from dimethylsulfate footprinting. Contacts with G in either DNA strand are noted by vertical dashes. The asterisks indicate GC base pairs at which contacts might be, but are not, detected. Nucleotides 10 and 60 in the standard numbering system for tRNA genes are indicated.

A wide range of box A-B separations is allowed (Hall et al., Cell 29:3–5 (1982); Carrara et al., Cell 27:371–379 (1981); Raymond et al., Nucleic Acids Res. 11:5969–5988 (1983); Dingermann et al., J. Biol. Chem. 258:10395–10402 (1983)) subject to certain limitations. Determining these limits is complicated by the nature of A and B box function and consensus: adventitious, weakly functioning substitutes, pseudoA and -B boxes, are capable of being exploited in the transcription of constructs that generate particularly unfavorable A-B box configurations. The application of two additional criteria helps in establishing spacing rules: 1. The separation between the transcription start site and box A remains constant, as already mentioned, for individual genes whose A-B separation varies between 21 and 365 bp (Baker et al., J. Biol. Chem. 261:5275–5282 (1986); Fabrizio et al., Proc. Natl. Acad. Sci. USA 84:8763–8767 (1987)). 2. Site-directed mutagenesis can unambiguously identify the ICR elements responsible for a designated transcript. Applying the first criterion to the S. cerevisiae tRNA$^{Leu}_3$ gene, A-B separations of 19 bp or less increasingly favor the utilization of a nearby upstream pseudoA box and a gene with contiguous A and B boxes utilizes such apseudoA box exclusively (Baker et al., J. Biol. Chem. 261:5275–5282 (1986)). Applying the second criterion, and S. cerevisiae TRNA$^{Leu}_3$ gene with an A-B box separation of 365 bp utilizes both of these widely separated elements as its ICR, although it is transcriptionally less active than its normal counterpart (Fabrizio et al., Proc. Natl. Acad. Sci. USA 84:8763–8767 (1987)). Very large A-B box separations have also been generated in a D. melanogaster tRNA$^{Arg}$ gene and in the VAI gene (Dingermann et al., J. Biol. Chem. 258:10395–10402 (1983); Cannon et al., Proc. Natl. Acad. Sci. USA 83:1285–1289 (1986)). A fine structure analysis of the S. cerevisiae tRNA$^{Leu}_3$ gene clearly shows that the relative helical orientation of the A and B boxes is unimportant and that separations of approximately 30–60 bp are optimal (Baker et al., J. Biol. Chem. 261:5275–5282 (1986)).

Truncated tRNA genes without a B box can initiate transcription in vitro at their normal site, albeit inefficiently (Carrara et al., Cell 27:371–379 (1981); Johnson et al., Mol. Gen. Genet. 197:55–61 (1984); Wilson et al., J. Mol. Biol. 183:153–163 (1985)). The absence of box B leaves such genes with a lower overall affinity for the transcription apparatus; very high DNA template concentrations or lower electrolyte concentrations are required to detect their residual activity (Dingermann et al., J. Biol. Chem. 258:10395–10402 (1983); Wilson et al., J. Mol. Biol. 183:153–163 (1985)). The properties of these B-less genes point to a curious relationship: in the ICR, the B box region is the major quantitative determinant of promoter strength, yet it is qualitatively dispensable. On the other hand, when box A is deleted, substitutes are readily found, yet their utilization determines a new, conjugate start point for transcription.

Recent observations on the effect of substituting acetate for chloride in analyzing variant S. cerevisiae tRNA$^{Glu}$ promoters in vitro have been thought to indicate that box A is not unconditionally required for transcription (Gabrielsen et al., Nucleic Acids Res. 15:5699–5713 (1987)). We instead interpret these results as being consistend with our conclusion that replacing box A with more weakly consensual pseudoboxes greatly lowers promoter strength, when assayed under conditions that are optimal for the normal gene. This work clearly makes the point that promoter strength needs to be analyzed over ranges of the relevant assay parameters (see also Wilson et al., J. Mol. Biol. 183:153–163 (1985)). If anions affect transcription activity (Leirmo et al., Biochemistry 26:2095–2101 (1987)), then nonphysiological chloride may be less-than-optimal for systematic analysis of promoter strength in vitro.

To ensure efficient expression of the modified tRNA$^{Lys3}$, the invention further provides for a gene encoding the modified tRNA where the gene is functionally linked to a promoter for in vivo expression or in vitro production of tRNA. A more preferred aspect of the invention is a promoter capable of promoting expression of the gene in human cells, in particular, where the human cells are human T-cells or macrophages. In a more preferred embodiment, the promoter is a pol III promoter.

To ensure efficient transcription of this mutated gene, flanking 5' sequences, which may contain enhancers for polymerase III-directed transcription may also be used. Also included were 3' flanking sequences consisting of the stop signal for polymerase III, and nucleotides required for processing, derived from the most efficiently expressed of the three cellular tRNAlys-UUU loci (Roy, K. L., et al., *Nuc. Acids Res.* 10, 7313–7322 (1982); Doran, J. L., et al., *Gene* 65, 329–336 (1988), which are hereby incorporated by reference). The mutant tRNA may also be designed to maintain essential features, in regions away from the 3' end, required for interaction with HIV-1 RT and NCp7 (Barat, C., et al., *Embo J* 8(11), 3279–85 (1989); Barat, C., et al., *J Mol Biol* 231(2), 185–90 (1993), which are hereby incorporated by reference).

The nucleic acid molecule encoding the tRNA molecule can be inserted into a suitable host cell. Various methods for transforming host cells are known in the art. One of the first methods was microinjection, in which DNA was injected directly into the nucleus of cells through fine glass needles. This was an efficient process on a per cell basis, that is, a large fraction of the injected cells actually got the DNA, but only a few hundred cells could be injected in a single experiment.

Several methods exist for introducing DNA into cells en masse. Chemical and physical methods include incubating the DNA with an inert carbohydrate polymer (i.e. dextran) to which a positively charged chemical group (i.e., diethylaminoethyl) had been coupled, calcium phosphate coprecipitation, or electroporation. DNA can also be incorporated into artificial lipid vesicles, liposomes, which fuse with the cell membrane, delivering their contents directly into the cytoplasm. Microinjection, the surest way to get DNA into cells, can now be performed with a computer-assisted apparatus that increases by 10-fold or more the number of cells that can be injected in one experiment.

Since the tRNA molecule is very small and has a low molecular weight, the tRNA can be placed directly on mammalian cells in culture as tRNA or as an oligonucleotide encoding the mutant tRNA gene and the tRNA will be taken into the cells by diffusion.

Retroviruses are RNA viruses which are useful for stably incorporating genetic information into the host cell genome. When they infect cello, their RNA genomes are converted to a DNA form (by the viral enzyme reverse transcriptase). The viral DNA is efficiently integrated into the host genome, where it permanently resides, replicating along with host DNA at each cell division. This integrated provirus steadily produces viral RNA from a strong promoter located at the end of the genome (in a sequence called the long terminal repeat or LTR). This viral RNA serves both as mRNA for the production of viral proteins and as genomic RNA for new viruses. Viruses are assembled in the cytoplasm and bud from the cell membrane, usually with little effect on the cell's health. Thus, the retrovirus genome becomes a permanent part of the host cell genome, and any foreign gene placed in a retrovirus ought to be expressed in the cells indefinitely.

Retroviruses are therefore attractive vectors because they can permanently express a foreign gene in cells. Moreover, they can infect virtually every type of mammalian cell, making them exceptionally versatile. Because of their versatility, retroviruses are also the vector of choice for gene therapy in which stable integration is desired. In the design and use of retroviral vectors, the vectors usually contain a selectable marker as well as the foreign gene to be expressed. Most of the viral structural genes are gone, so these vectors cannot replicate as virugeg on their own. To prepare virus stocks, cloned proviral DNA is transfected into a packaging cell. These cells usually contain an integrated provirus with all its genes intact, but lacking the sequence recognized by the packaging apparatus. Thus, the packaging provirus produces all the proteins required for packaging of viral RNA into infectious virus particles but it cannot package its own RNA. The packaging system may allow use of a variety of viral envelopes to alter viral tropism, and ability to infect human cells. Examples include retroviral vectors using amphotropic, HIV-1/2, SIV, Gibbon Ape Leukemia Virus ("GALV") or Vesicular Stomatis Virus ("VSV") envelope. Vector packaging systems and/or backbones may be derived from various sources such as MoMuLV, or even lentiviruses such as HIV-1, SIV, etc. RNA transcribed from the transfected vector is packaged into infectious virus particles and released from the cell. The resulting virus stock is termed helper-free, because it lacks wild-type replication-competent virus. This virus stock can be used to infect a target cell culture. The recombinant genome is efficiently introduced, reverse-transcribed into DNA (by reverse transcriptase deposited in the virus by the packaging cells), and integrated into the genome. Thus, the cells now express the new virally introduced gene, but they never produce any virus, because the recombinant virus genome lacks the necessary viral genes. Alternative viral vectors, which may be used in place of retroviruses to produce stable integration include the adenoassociated virus vectors (AAV) (Flotte, et al., *Gene Ther.* 2, 29–37 (1995); Zeitlin, et al., *Gene Ther.* 2, 623–31 (1995); Baudard, et al., *Hum. Gene Ther.*, 7, 1309–22 (1996); which are hereby incorporated by reference). For a review of retrovirus vectors, see Austin, *Gene Ther.* 1 Suppl 1, S6–9 (1994) and Eglitis, *Blood* 71, 717–22 (1988), which are hereby incorporated by reference. Other viral vectors are derived from adenovirus, herpesviruses, etc.

The invention, therefore, provides viral vectors which carry the gene encoding the modified tRNA molecule. As a more preferred embodiment, the viral vector is a retroviral vector.

The nucleic acid molecule encoding the tRNA molecule can thus be inserted directly into a host cell or into an intermediate expression vector. As indicated above, various expression vectors are known in the art, including plasmids, viral vectors, and bacteriophage vectors. The host cell to be transformed with the nucleic acid molecule may be most amenable to transformation with a particular type of expression vector. Plasmid vectors readily transform bacterial host cells. Viral vectors readily transform many mammalian cells.

The nucleic acid molecule is inserted into the expression vector using standard cloning procedures readily known in the art. This generally involves the use of restriction enzymes and DNA ligases, as described by Maniatis et al. (1982), which is hereby incorporated by reference. U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Suitable vectors include, but are not limited to, the following vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993)), pQE, pIH821, pGEX, pET series (see Studier et al. (1990)), and any derivatives thereof.

A variety of host-vector systems may be utilized to introduce and express the tRNA molecule. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria (e.g., *Agrobacterium tumefaciens*). The expression elements of these vectors vary in their strength and specificities. Depending upon the host-vector system utilized, any one of a number of suitable transcription and translation elements can be used.

Once the isolated nucleic acid molecule encoding the tRNA has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, and the like. Expression systems may also be used for in vitro transcription.

Biological markers can be used to identify the cells carrying recombinant DNA molecules. In bacteria, these are commonly drug-resistance genes. Drug resistance is used to select bacteria that have taken up cloned DNA from the much larger population of bacteria that have not. Similar genes allowing drug selection are available for eukaryotic cells such as:

aminoglycoside phosphotransferase ("APH"), using the drug G418 for selection which inhibits protein synthesis; the APH inactivates G418;

dihydrofolate reductase ("DHFR"): Mtx-resistant variant, using the drug methotrexate ("Mtx") for selection which inhibits DHFR; the variant DHFR is resistant to Mtx;

hygromycin-B-phosphotransferase ("HPH"), using the drug hygromycin-B which inhibits protein synthesis; the HPH inactivates hygromycin B;

thymidine kinase ("TK"), using the drug is aminopterin which inhibits de novo purine and thymidylate synthesis; the TK synthesizes thymidylate;

xanthine-guanine phosphoribosyltransferase ("XGPRT"), using the drug mycophenolic acid which inhibits de novo GMP synthesis; XGPRT synthesizes GMP from xanthine; and adenosine deaminase ("ADA"), using the drug 9-β-D-xylofuranosyl adenine ("Xyl-A") which damages DNA; the ADA inactivates Xyl-A.

Another embodiment of the invention is a modified tRNA$^{Lys3}$ molecule for inhibiting HIV replication. The tRNA$^{Lys3}$ molecule which is modified to inhibit interaction of the tRNA$^{Lys3}$ molecule with HIV-1 reverse transcriptase or HIV-1 RNA template. The modification is introduced outside of the acceptor stem of the tRNA$^{Lys3}$ molecule. Mutations in specific regions of the tRNA$^{Lys3}$ molecule, such as the TΨC loop and the anticodon loop, which have been identified as interacting with reverse transcriptase are preferred.

The invention further provides a method of inhibiting HIV infectivity in human cells. A modified tRNA molecule as described in the various embodiments above, is introduced into human cells. The modified tRNA molecule is a small molecular weight nucleic acid and may also be taken up directly by the cells if provided exogenously. Alternatively, the gene encoding the modified tRNA molecule may be introduced into the cells and the tRNA molecule is then produced from the gene.

A more preferred aspect of this method is where the human cells are T-cells or human hematopoietic stem cells. In a most preferred embodiment, the stem cells are eripheral blood or bone marrow derived CD34$^+$ stem cells.

The invention may be practiced by removing the cells to be transduced from the body and transducing them in vitro. In particular, blood or bone marrow may be removed from a patient for transduction and reintroduction. Another preferred embodiment is where the gene encoding the modified tRNA molecule is introduced into human cells in vivo.

In vivo introduction of the gene encoding the tRNA molecule can be accomplished by contacting cells with a viral vector carrying the gene encoding the modified tRNA molecule. A more preferred embodiment is where the viral vector is a retroviral vector.

The gene encoding the modified tRNA molecule may be introduced into human cells from an individual with acquired immunodeficiency syndrome, an individual infected with the HIV virus but not yet having AIDS.

EXAMPLES

Example 1

Experimental Procedures
tRNA Constructs for Studies in Vitro

Figure 1B:
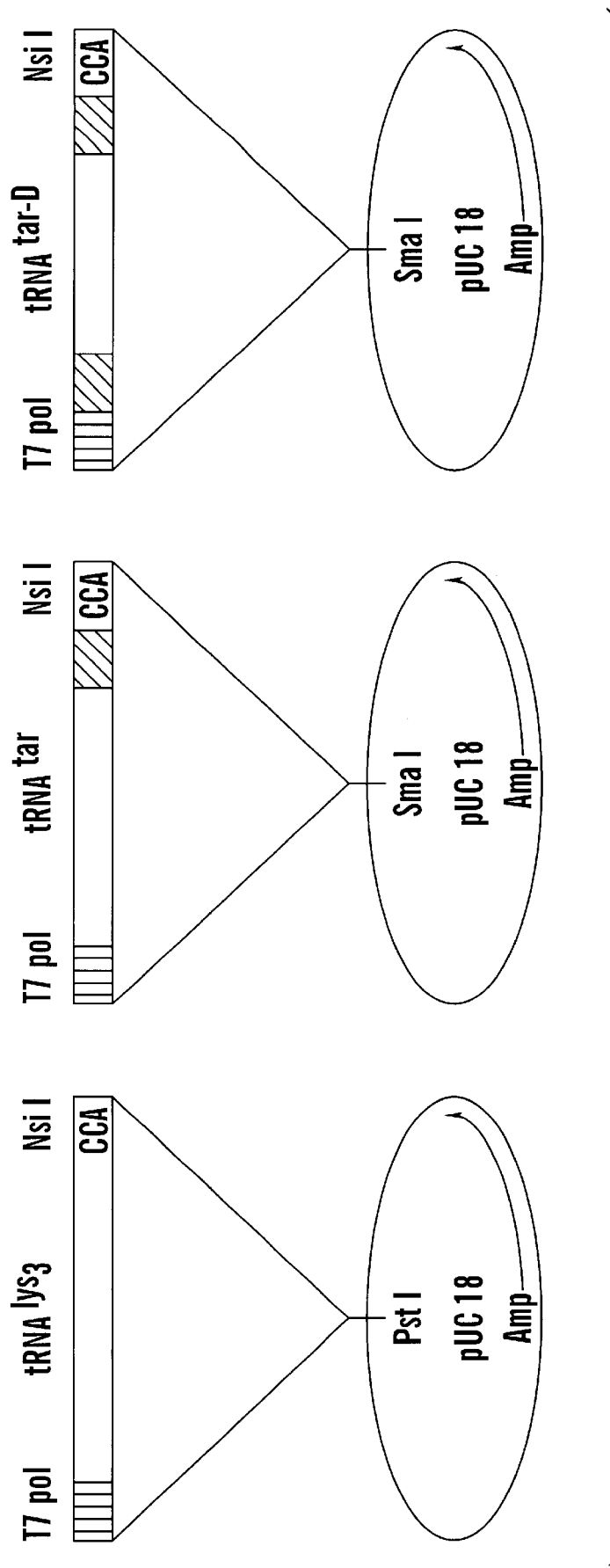
FIG. 1B schematically represents the plasmids used for in vitro transcription of tRNA$^{Lys3}$ tRNA$^{tar}$, and tRNA$^{tarD}$. The tRNAtarD coding sequence plus an additional 20 flanking nucleotides at its 5' end and 130 nucleotides at its 3' end was cloned into a double copy-retroviral vector N2A (Sullenger, B. A., et al., Cell 63, 601–608 (1990), which is hereby incorporated by reference). When packaged in the PG13 retroviral packaging cell line and transduced into target cells, the vector carries 2 copies of tRNAtarD at both the 5' and 3' long terminal repeats.
Figure 1C:
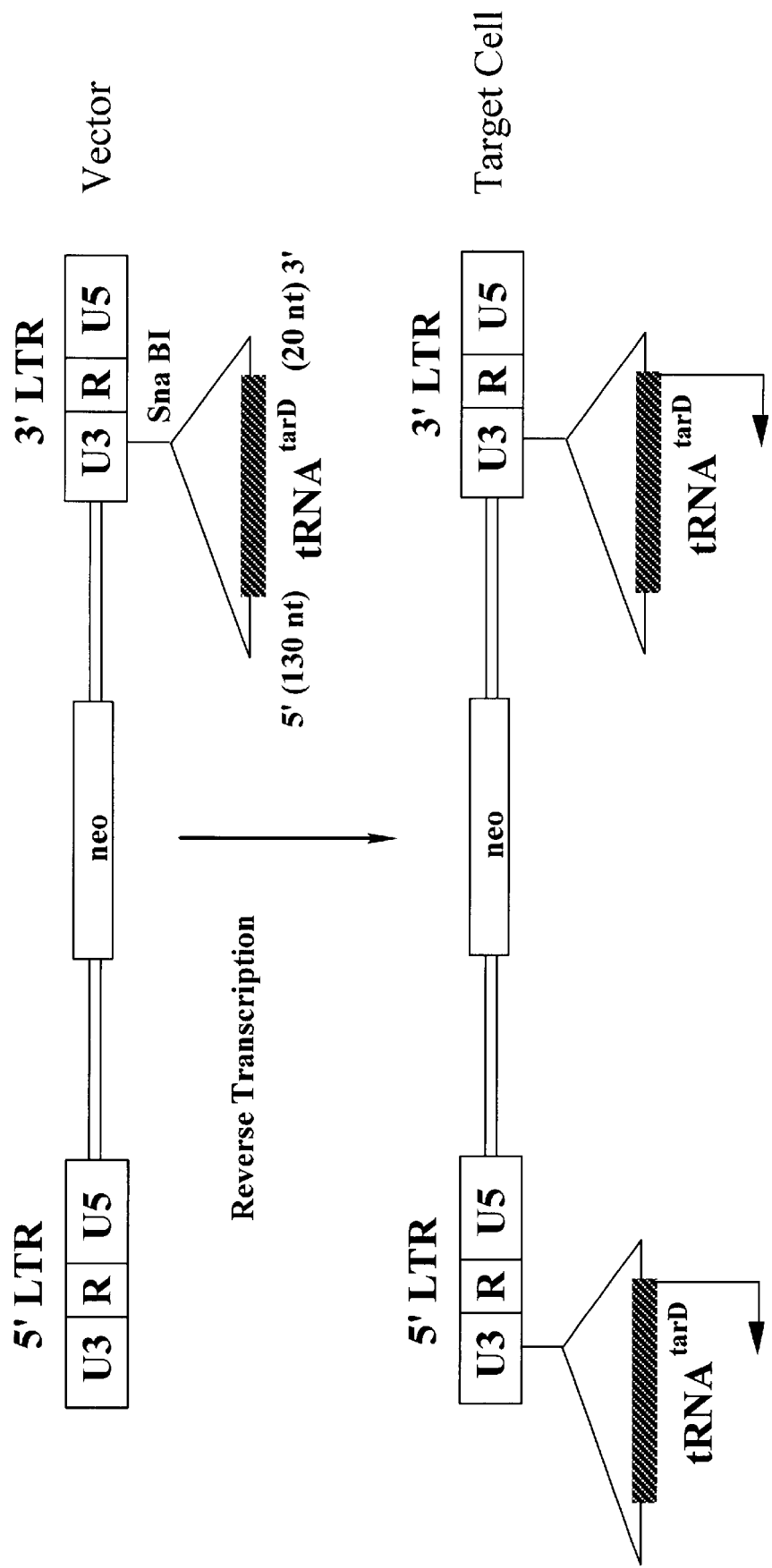
FIG. 1C depicts the retroviral vector, N2A-$^{tarD}$, which is used for expression in vivo of tRNA$^{tarD}$.

Several plasmids, pUClys, pUCtar, pUC$^{tarD}$, were constructed containing coding sequences for both tRNA$^{Lys3}$ and two mutant tRNAs, designated tRNA$^{tar}$ and tRNA$^{tarD}$, downstream of the T7 promoter as shown in FIG. 1. Coding sequences for tRNA$^{Lys3}$ were synthesized by annealing and extending two oligonucleotides: left primer 5'-AATTGCTGCAGTAATACGACTCACTATAGCCCGGA TAGCTCAGTcGGTAGAGCATCA GACTTTTAATCTGAGGGTCCAGGGTTCAAG-3' (SEQ ID NO: 3); and right primer 5'-CTAAGCTGCAGATGCATGGCGCCCGAACAGGGA CTTGAACCCTGGACCCT 3' (SEQ ID NO: 4) at 70° C. for 15 mninutes followed by 37° C. for 30 minutes in 1X PCR buffer using vent polymerase (NEB). The resulting PCR fragment was digested with Pst I and cloned into the Pat I site of pUC120 to yield pUClys. pUCtar, an intermediate construct, was obtained by amplification of pUClys using vent DNA polymerase (NEB) and the primer pair 5'-GTAATACGACTCACTATA-3' (SEQ ID NO: 5) and 5'-CTAAGCTGCAGATGCATGGTTAGACCACAGGGAC TTGAACCCTGGACCCT-3' (SEQ ID NO: 6) in the presence of 200 μM dNTP, according to manufacturer's instructions. PCR was performed at 94° C. for 30 sec., 52° C. for 30 sec. and 72° C. for 30 sec., and repeated for 35 cycles. The tRNA$^{tarD}$ sequences were generated by amplification of pUclys using the primer pair: left 5'-AATTGCTGCAGTAATACGACTCACTATATAGACCA TAGCTCAGTCGGTAGAGCA-3' 5'(SEQ ID NO: 7) and 5'-CTAAGCTGCAGATGCATGGTTAGACCACAGGGAC TTGAACCCTGGACCCT-3' (SEQ ID NO: 8). Conditions for PCR were as described for tRNAtar. Both PCR fragments were then cloned into Sma I site of pUC18 to yield pUCtar and pUC$^{tarD}$, respectively.
Vector Construction The tRNA$^{Lys}$UUU gene (Roy, K. L., et al., *Nuc. Acids Res.* 10, 7313–7322 (1982), which is hereby incorporated by reference) with 5' and 3' flanking sequences was obtained by amplification of DNA extracted from HeLa cells using the primers:
5'-TCGCCGAGATAAGCTTCAGCCTCTACTATGGTACAG-3' (SEQ ID NO: 9) and 5'-ATAATAGCACAAGCTTTATTACCCTCCACCGTCGTT-3' (SEQ ID NO: 10). The reagents and conditions for PCR were the same as described above except that the 35 cycles were carried out at 94° C. for 1 min, 55° C. for 1 min, and 72° C. for 1 min. The PCR fragments were then digested with Hind III and cloned into the Hind III site of pBluescript-KS vector, to yield pM13$^{Lys3}$. The tRNA$^{tarD}$ gene, including 20 nucleotides upstream and 130 nucleotides downstream flanking the human tRNA$^{Lys}$-UUU gene, was obtained by PCR amplification using two primer pairs: 1L, 5'-GTAAAGCTCTCGTGAAGATAGACCATAGCTCAGT CGGTAGAGC-3' (SEQ ID NO: 11); 1R, 5'-CCAAAAGCAAAGACATGCCGCTTAGACCACAGG GACTTGAACCCTGGAC-3' (SEQ ID NO: 12) and 2L, 5' GTCCAGGGTTCAAGTCCCTGTG-GTCTAAGCGGCATGTCTTTGCTTTTGG 3' (SEQ ID NO: 13); 2R, 5' ATAATAGCACAAGCTTTATTACCCTC-CACCGTCGTT 3' (SEQ ID NO: 14). The first amplification was done using the pM13$^{Lys3}$ DNA template and primers 1L and 1R, resulting in fragment A. A second amplification was carried out using pM13$^{Lys3}$ and primers 2L and 2R, giving rise to fragment B. Both A and B fragments were then agarose gel purified. A third PCR reaction was performed using a mixture of purified A and B fragments as templates. Primers 1L and 2R were used to generate a tRNA$^{tarD}$ sequence containing 5' and 3' flanking sequences required for correct transcription and processing by polymerase III. The final PCR fragment was cloned into the blunted Xho I site of pAC7, an AAV derived vector (Lebkowski, J. S., et al., Mol. Cell Biol 8, 3988–3996 (1998), which is hereby incorporated by reference), resulting in pACtarD. The sequence was then verified. tRNA$^{tarD}$ coding sequences were excised from pACtarD by Hind III and Nco I digestion. After complete filling of the ends formed by Hind III and Nco I, the fragment was subcloned into the Sna BI site of the vector pN2A, (Sullenger, B. A., et al., Mol. Cell Biol. 12, 6512–6513 (1990), which is hereby incorporated by reference) resulting in the retroviral vector pN2A-tarD (FIG. 1C), and sequence and orientation were confirmed by dideoxy sequencing.

The vector PSP-PBS was constructed by subcloning a 0.9 kb, Sca I to Nsi I fragment from pNL4-3 (Adachi, A., et al., Journal of Virology 59, 284–291 (1986), which is hereby incorporated by reference) into the bacterial vector, pSP-73 (Promega Corp., Madison, Wis.) previously digested with Pvu II and Nsi I. The restriction fragment from pNL4-3 includes nucleotides −133 to +386 of the flanking sequences and 5' LTR region of HIV-1-NL4-3 (Adachi, A., et al., Journal of Virology 59, 284–291 (1986), which is hereby incorporated by reference).

Interaction of tRNA Transcribed in Vitro with HIV-1 Reverse Transcriptase pUClys, pUCtar, and pUCtarD were linearized by Nsi I digestion to generate a 3' CCA end and transcribed by T7 polymerase using reagents and conditions supplied with Promega T7 transcription was carried out in the presence of 10 µCi $^{32}$P-CTP. Radiolabeled RNAs were gel purified according to the method described previously (Oommen, A., et al., Mol Cell Biol 12(2), 865–75 (1992), which is hereby incorporated by reference). In a 20 µl reaction, 200 fmol of labeled tRNA were incubated with either 800 fmol of purified HIV-1 reverse transcriptase (L. Martin, Wellcome) or 1 µg of BSA (Sigma Chemical Co., St. Louis, Mo.) in the presence or absence of 1 to 100 molar excess of the following unlabeled competitor RNAs: yeast tRNA$^{Phe}$ (Sigma Chemical Co.), tRNA$^{Lys}$, tRNA$^{tar}$, and tRNA$^{tarD}$, all transcribed in vitro, in a buffer containing 10 mM DTT, 40 mM Tris-HCl (pH 8.3), 60 mM NaCl, and 6 mM MgCl$_2$. The mixtures were incubated at 37° C. for 30 min, and then subjected to electrophoresis in a 4% nondenaturing acrylamide gel, in buffer containing 1x TBE and glycerin. After drying in a vacuum, the gel was exposed to Kodak X-AR film overnight.

Retroviral Vectors

The tRNA$^{tarD}$ fragment was subcloned into the Sna BI site within the multicloning site in the 3'LTR of the vector pN2A (Sullenger, B. A., et al., Mol. Cell Biol. 12, 6512–6513 (1990), which is hereby incorporated by reference) resulting in N2A-tarD (FIG. 1C). After viral passage and reverse transcription of pN2A-tarD, duplication of the tarD sequences into the 5'LTR occurs leading to a provirus containing a double copy of the tRNA$^{tarD}$ expression cassette (FIG. 1C). The control vector pLN, a MoMuLV-based retroviral vector containing the neomycin resistance gene (neo$^R$) expressed from the MoMuLV-LTR, was constructed and packaged in the laboratory of A. Dusty Miller (Fred Hutchinson Cancer Center, Seattle, Wash.).

Cell Lines

The GP+E-86 ecotropic packaging cell line was a generous gift from A. Bank (Columbia University; New York, N.Y.). The PA317 amphotropic packaging cell line and NIH3T3 fibroblasts were obtained from the American Type Culture Collection. The T-cell lines MT-2 and CEM were obtained from the AIDS Research and Reference Reagent Program of the National Institutes of Health (Rockville, Md.). PA317 and NIH3T3 cells were grown in DMEM supplemented with 10% fetal calf serum (FCS) and 10% calf serum, respectively. GP+E-86 were grown in DMEM supplemented with 10% newborn calf serum, hypoxanthine (15 µg/ml), xanthine (250 µg/ml), and mycophenolic acid (25 µg/ml). To prepare viral supernatant, the medium was changed to DMEM with 10% FCS. MT-2 cells were maintained in IMDM containing 10% FCS.

Retroviral Packaging and Transduction into MT-2 Cells

The vector pN2A-tarD was transfected into the ecotropic packaging cell line GP+E-86 using lipofection (GIBCO-BRL; Bethesda, Md.). Transfected cells were selected in 0.5 mg/ml G418 (Geneticin; GIBCO-BRL). Virus-containing supernatant from the GP+E-86 cells was collected and used to transduce PA317 amphotropic packaging cells, and the cells selected in 0.5 mg/ml G418. High-titer clones were identified by measuring the transfer of G418 resistance using serially diluted supernatant to NIH3T3 fibroblasts, and supernatant from these clones was used to transduce MT-2 cells and CEM cells (ATCC)

To transduce MT-2 cells, LN and N2A-tarD vector-producing PA317 cells were irradiated at 40 Gy and plated at 2×10$^6$ cells per 100 cm$^2$ plate 24 hours before the addition of 1×10$^6$ MT-2 cells. Cocultivation was carried out in the presence of 8 µg/ml of polybrene for 48 hours. Non-adherent MT-2 cells were collected, and a second round of cocultivation over irradiated vector-producing fibroblasts was performed. Subsequently, transduced MT-2 cells were selected in 0.5 mg/ml G418, and subcloned by limiting dilution in 96-well plates.

Detection of tRNA Sequences by Polymerase Chain Reaction

DNA from MT-2 and N2A-tarD-transduced MT-2 (MT-2-tarD) cells were extracted as follows. Cells were pelleted by low-speed centrifugation and washed once with phosphate-buffered saline. Cells were lysed in 3 ml of a solution containing 500 μg/ml of proteinase K and 50 μg/ml of RNase A, 0.15 M NaCl, 0.01 M Tris-HCl (pH 7.4), 0.1 M EDTA (pH 8.0), and 0.1% SDS. Following incubation at 56° C. for 3 h, the aqueous phase was gently extracted with an equal volume of phenol/CHCl$_3$/isoamyl alcohol mixture 925:24:1) twice followed by an equal volume of CHCl$_3$/isoamyl alcohol (24:1), and DNA was ethanol-precipitated. DNA was harvested using a sealed-curved Pasteur pipette, briefly rinsed in 70% of ethanol and air dried. The DNA was dissolved in 300μ of TE buffer (10 mM Tris-HCl, pH 7.8, 1 mM EDTA). PCR reaction conditions were as described by the manufacturer (Perkin Elmer, Norwalk, Conn.). Each reaction was conducted in a final volume of 50 μl containing 1.25 U of Taq DNA polymerase and a total of 300 ng of tRNA$^{tarD}$-specific primers (sense: 5'-TAGACCATAGCTCAGTCGGT-3' (SEQ ID NO: 15) and antisense: 5'-TGGTTAGACCACAGGGACTT-3') (SEQ ID NO: 16) or 300 ng of tRNA$^{Lys3}$ specific primers (sense: 5'-GCCCGGATAGCTCAGTCGGT-3' (SEQ ID NO: 17) and antisense: 5'-TGGCGCCCGAACAGGGACTT-3' (SEQ ID NO: 18)). Thermocycling temperatures used were: initial denaturation at 94° C. for 5 min, annealing at 60° C. for 2 min, and extension at 72° C. for 2 min, followed by cycling at 94° C. for 1 min, 60° C. for 2 min, and 72° C. for 2 min for a total of 30 cycles. 10 μl of the amplified PCR product was subjected to electrophoresis in a 2% agarose gel. Following electrophoresis at 120 volts for 2 hours, the PCR products were visualized by ethidium bromide staining and UV transillumination.

RT-PCP for Assay of tRNA$^{tarD}$ Expression

Total RNA was extracted from parental MT-2 and MT-2/TARD cells using the acid guanidinium isothiocyanate/phenol-chloroform method (AGPC) (Chromczynski, P., et al., *Analytical Biochemistry* 162, 156–159 (1987), which is hereby incorporated by reference). Cells were washed once in phosphate-buffered saline, pH 7.2 (GIBCO-BRL), and disrupted by mixing with 3 ml of solution D containing 4 M guanidinium isothiocyanate, 25 mM sodium-citrate, pH 7.0, 0.5% sarcosyl. Following extraction with 300 μl of 3 M sodium acetate (pH 5.2), 3 ml phenol (pH 4.3), and 600 μl of CHCl-IAA (24:1), the aqueous phase containing RNA was transferred to a fresh tube, mixed with an equal volume of isopropanol, and then placed at 20° C. for 2 h to precipitate the RNA. The precipitated RNA was pelleted by centrifugation (10,000 g, 30 min) at 4° C., dissolved in 500 μl of solution D, treated with DNase, and then precipitated at −20° C. overnight by the addition of an equal volume of isopropanol. The RNA was recovered by centrifugation and redissolved in small amount of diethylpyrocarbonate (DEPC) treated water at 65° C. for 5 min. The amount of nucleic acid was quantitated by measurement of $A_{260}$, and the RNA integrity confirmed in a 1% agarose gel.

The reverse transcriptase reaction was carried out using MoMuLV reverse transcriptase (GIBCO-BRL) following manufacturer's recommendations for first strand synthesis, using 100 ng of antisense primers. Amplification of the reverse transcribed cDNA was performed under the same conditions as described above for DNA PCR except that only 1 μl of reverse transcribed cDNA (RT-reaction product from step 1) was used as the DNA template. The amplified cDNA was then subjected to agarose gel electrophoresis.

Cells and Virus

Parental MT-2, MT-2/LN cells which were transfected with retroviral vector alone (no tRNA$^{tarD}$ expression), and the MT-2/TARD cells were compared for ability to support HIV-1 replication. Cells were routinely grown in Iscove's medium (GIBCO-BRL) containing 10% fetal bovine serum (FBS) and 1× of Penn/Strep at 37° C. The virus strain used in this study was HIV-IIIB, which was prepared and titered in MT-2 cells.

TCID$_{50}$ Assay

Cells were seeded into 96-well plates at 5×10$^3$ cells/well. HIV-IIIB virus stock was serially diluted 10-fold in Iscove's medium containing no FBS. Using 4–6 wells per dilution for each cell line, 0.1 ml/well of each virus dilution was inoculated. Control wells received the same amount of medium. Infected cultures were examined daily for syncytia formation and viral titers determined at days 5 and 10 postinfection according to the method described by Reed and Muench (Reed, L. J., et al., *Am. J. Hyq.* 27, 493–497 (1983), which is hereby incorporated by reference).

Infections and Viral p24 Assay

For each infection, a total of 1×10$^4$ cells in exponential growth phase were harvested and washed once with medium and pelleted. The cell pellet was then resuspended in 1 ml of diluted HIV-IIIB stock containing 10 TCID$_{50}$ units of virus. After adsorption at 37° C. for 2 h 10 ml of medium was added, and the cells were pelleted by centrifugation. They were then resuspended in 15 ml of Iscove's and 10% FCS medium, and transferred into a 25 cm$^2$ flask. Duplicate infections per cell line were employed in each challenge assay, and the infected cultures were incubated at 37° C. Every other day beginning from day 2 post infection, 0.5 ml of culture supernatant was removed from the flasks, and virus replication was monitored by measuring the production of p24 viral antigen in culture supernatant using an HIV-1 p24 antigen capture ELISA assay (Coulter Immunology, Hialeah, Fla.). MT-2/LN cells were simultaneously infected as controls.

RNA-dependent DNA Polymerase Assays

Template RNAs comprising HIV-1 genome sequences for RNA dependent DNA polymerase assays in vitro were generated from the plasmid clone, pSP-PBS (see "Vector construction" above). They were made by run-off transcription following restriction digestion by using previously described procedures. Template RNA 1, 545 nucleotides long, was generated by transcription in vitro of an Xmn I restriction fragment of pSP-PBS using T7 RNA polymerase. Template RNA 1 encompassed nucleotides −133 to +386 of the flanking sequences and 5' LTR region of pNL4-3 (Adachi, A., et al., *Journal of Virology* 59, 284–291 (1986), which is hereby incorporated by reference). In addition, its 5' end contained 26 nucleotides from the multiple cloning site of pSP-73. Template RNA 2 was generated following restriction digestion of the plasmid pSP-PBS with Hind III followed, by transcription in vitro using T7 RNA polymerase. Template RNA 2 contained the region of the genomic RNA from −133 to +81, 240 nucleotides in length. This sequence does not include the PBS. DNA primers 1, 2 and 3 were complementary to regions of the template RNAs corresponding to HIV-1 genomic positions +191 to +209, +59 to +78, and +22 to +41, respectively. Conditions for annealing of the RNA templates with the DNA primers, tRNA$^{Lys3}$ or tRNA$^{tarD}$ were as previously described (Palaniappan, C., et al., *J Biol Chem* 270(9), 4861–4869 (1995), which is hereby incorporated by reference). The RNA template and the respective primers were annealed in 10 mM Tris-HCl (pH 8.0), 1 mM EDTA, and 80 mM KCl with a 10:1 molar ratio of primer to template. Similarly, RNA dependent DNA polymerase assays were carried out as before with slight modifications (Palaniappan, C., et al., *J Biol Chem* 270(9), 4861–4869 (1995), which is hereby incorporated by reference). Final reaction mixtures contained 50 mM Tris-HCl (pH 8.0), 1 mM dithiotreitol, 1.0 mM EDTA, 34 mM KCl, 6 mM MgCl$_2$, 2 nM substrate, 50 µM unlabeled dNTPs and 4 units of recombinant purified HIV-1 RT (Genetics Institute (Cambridge, Mass.)). This RT has native heterodimeric structure. When examined on SDS-PAGE electrophoresis, it was essentially homogeneously pure. It is free of detectable nuclease and polymerase contaminants, and has a specific activity of 40,000 units/mg. One unit is defined as the amount required to incorporate 1 nmol of dT into a poly(rA)-oligo(dT) template in 10 min at 37° C. The RT was preincubated with the substrate for 5 min at 37° C. The reaction was initiated by the addition of MgCl$_2$ and dNTPs, incubated for 15 min and terminated with 25 µl of termination mix (90% formamide (v/v), 10 mM EDTA (pH 8.0), and 0.1% each of xylene cyanol and bromophenol blue). For some experiments, DNA synthesis was performed in the presence of α$^{32}$P-dCTP. When radiolabeled tRNA primers were employed, unlabeled dNPTs were used in the synthesis reaction. Reaction products were resolved on 6% urea polyacrylamide denaturing gels followed by autoradiography.

Analysis of HIV-1 Virions

Cells were harvested by low speed centrifugation (3,000 rpm, 30 min). Recovered supernatant was filtered through a 0.22 µm filter, and virus present in the filtrate was concentrated and purified by sucrose gradient centrifugation prior to isolation of viral RNA. HIV-1-IIIB produced from MT-2/LN cells was similarly prepared for control analysis. Total viral RNA was extracted from purified viral pellets using the acid guanidinium isothiocyanate-phenol-chloroform ("AGPC") method as described above for total cellular RNA preparation (Chromczynski, P., et al., *Analytical Biochemistry* 162, 156–159 (1987), which is hereby incorporated by reference). RNA concentration was determined by A$_{260}$, and RNA integrity was verified by electrophoresis on a 1% agarose gel. Then analysis of viral RNAs for mutant tRNA$^{tarD}$ was conducted by RT-PCR protocol (see above). For each RT-PCR reaction, 0.2 µg of viral RNA was amplified by the tRNA$^{tarD}$-specific primers, and amplified products were subjected to gel electrophoresis. Amplification of the viral RNAs with tRNA$^{Lys3}$-specific primers was also performed as a control.

Example 2
Binding of tRNA Mutants to HIV RT

Figure 2:
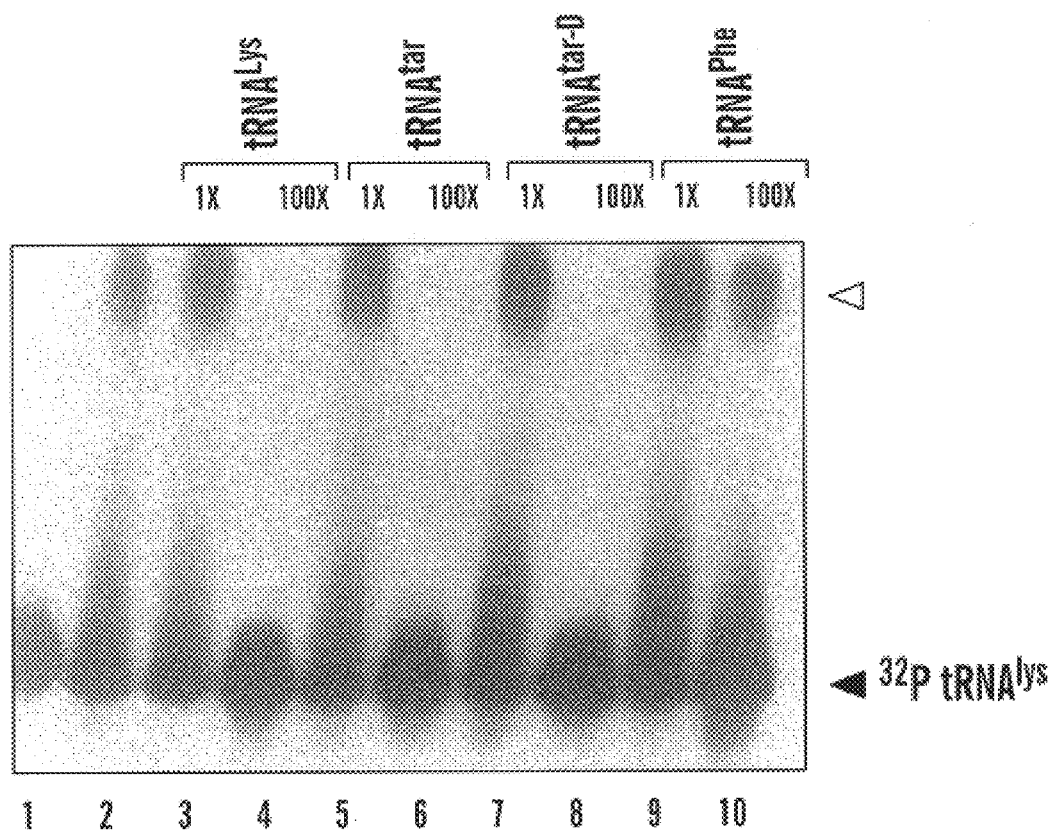
FIG. 2 shows the results of competition experiments where the ability to initiate transcription of HIV-1 RT by tRNA$^{Lys3}$ was challenged with tRNA$^{tar}$ or tRNA$^{tarD}$. Purified 32p-labeled tRNA$^{Lys3}$, transcribed in vitro (lane 1), was incubated with purified recombinant HIV-1 RT in the presence of either one-fold or 100-fold molar excess of unlabeled tRNA$^{Lys3}$, tRNAtar, tRNAtarD, transcribed in vitro, or yeast tRNA$^{Phe}$, tRNA$^{Lys3}$ forms a complex with HIV-1 RT in the absence of any competitor (lane 2) and in the presence of one fold molar excess of either itself (lane 3) tRNAtar (lane 5), or tRNAtarD (lane 7). Both tRNAtar (lane 6) and tRNAtarD (lane 8) in 100-fold molar excess compete for the binding of HIV-1 RT to tRNA$^{Lys3}$ to a similar degree to that seen with tRNA$^{Lys3}$ itself (lane 4), suggesting similar affinity to HIV-1 RT. In contrast, tRNA$^{Phe}$ in 100-fold molar excess did not compete effectively for HIV RT binding (lane 10).

HIV-1 RT has been reported specifically to recognize the tRNA$^{Lys3}$ anticodon region (Arts, E., et al., *J. Biol. Chem.* 269, 14672–14680 (1994); Barat, C., et al., *Embo J* 8(11), 3279–85 (1989); Barat, C., et al., *J Mol Biol* 231(2), 185–90 (1993), which are hereby incorporated by reference). Seven nucleotides of the 3' sequence of tRNA$^{Lys3}$ were substituted to produce a sequence complementary to the conserved TAR region of HIV-1, designated tRNAtar (FIG. 1A). In the second mutant, six additional substitutions were made in 5' sequences complementary to the 3' mutations to restore tRNA secondary structure. This mutant was designated tRNA$^{tarD}$ (FIG. 1A). Both tRNA$^{tar}$ and tRNA$^{tarD}$ retained wild type anticodon stem-loop sequences (FIG. 1A). To determine whether substitutions within either the 3' primer binding sequences or the structure of the acceptor stem of tRNA would affect the affinity of RT for mutant tRNAs, tRNA$^{Lys3}$, tRNA$^{tar}$ and tRNA$^{tarD}$, were transcribed in vitro and assayed for binding by gel retardation assay (FIG. 2). tRNA$^{tar}$ and tRNA$^{tarD}$ bound to purified HIV-1 RT with similar affinity to that of tRNA$^{Lys3}$ as determined by gel retardation of a radiolabeled RNA substrate. As shown in FIG. 2, binding of HIV-1 RT to tRNA$^{Lys3}$ could be effectively competed by 100-fold molar excess of tRNA$^{Lys3}$, tRNA$^{tar}$, or tRNA$^{tarD}$ (lanes 4, 6, and 8), but was poorly competed by 100-fold molar excess of tRNA$^{Phe}$ (lane 10). Additional gel-shift experiments showed that tRNA$^{tar}$ and tRNA$^{tarD}$ bound efficiently to HIV-1 RT, but not to MoMuLV RT. The ability of tRNA$^{Lys3}$-derived mutants to bind RT is likely retained due to the preserved anticodon region of tRNA, which is important in recognition by HIV-1 RT (Barat, C., et al., *J Mol Biol* 231(2), 185–90 (1993), which is hereby incorporated by reference).

Figure 3A:
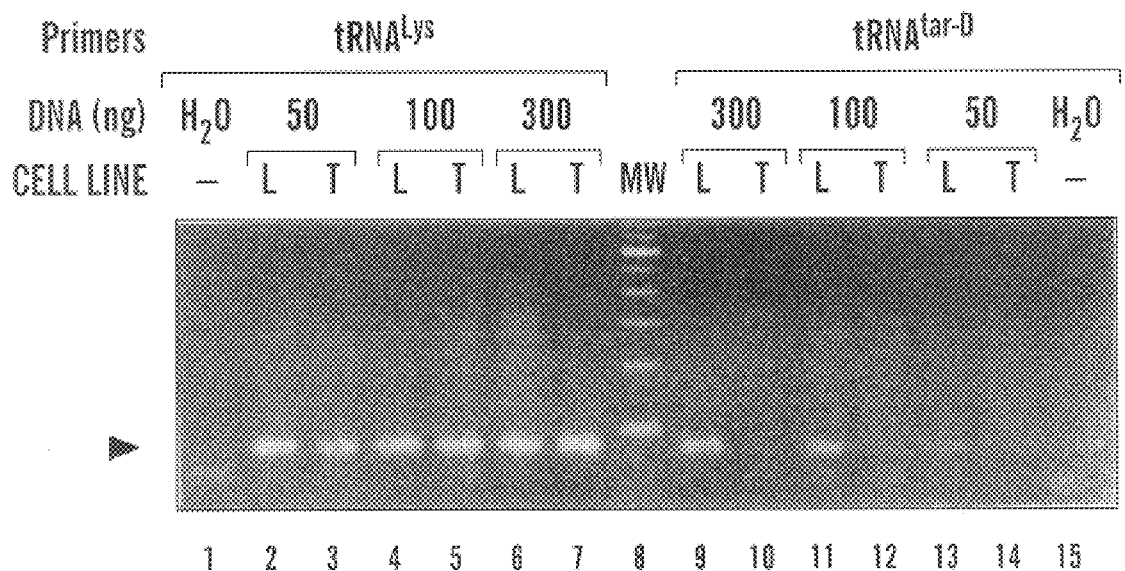
FIG. 3A depicts the detection of DNA sequences encoding tRNA$^{Lys3}$ and tRNAtarD in control MT-2 ("L" lanes) and transduced MT-2/TARD ("T" lanes) cells. DNA was extracted from cells, and indicated amounts of DNA or H$_2$O were amplified with tRNA$^{Lys3}$-or tRNAtarD-specific primers.

Example 3
Transduction of MT-2 Cells with a Retroviral Vector Encoding tRNA$^{tarD}$ An MT-2 T-cell line was transduced with the retroviral vector, N2A-tarD (FIG. 1C), containing tRNA$^{tarD}$ coding sequences. Assays for polymerase III-directed transcription in vitro using Jurkat-derived T-Cell extracts, and the N2A-tarD vector coding sequences, resulted in transcription and correct processing of tRNA$^{tarD}$. Following G418 selection of transduced cells, DNA and RNA were extracted from bulk G418 selected cells and from cloned cell lines. Mutant tRNA sequences in MT-2/TARD cells were detected using a selective PCR procedure. Although there are shared sequences between primers used for tRNA$^{Lys3}$ and primers for tRNA$^{tarD}$ (13 out of 20 nt), detection of either tRNA$^{tarD}$ DNA or RNA was specific using tarD primers as shown in FIG. 3A, lanes 9, 11 and 13, for DNA PCR and FIG. 3B, lanes 4 and 9, for RT-PCR under the conditions employed. As shown in FIG. 3A, mutant tRNA$^{tarD}$-coding sequences were detected using tRNA$^{tarD}$-specific primers in N2A-tarD transduced MT-2/TARD cells (lanes 9, 11 and 13), but not in DNA prepared from parental MT-2 cells (lanes 10, 12, and 14). When PCR was performed using primers specific for wild type tRNA$^{Lys3}$, signals with similar intensity were observed in all the cell lines examined (FIG. 3A, lanes 2, 4, and 6 for MT-2 and lanes 3, 5, and 7 for MT-2/TARD). Therefore, despite the small PCR product size of about 76 bp, and partial homology to tRNA$^{Lys3}$, the mutant tRNA$^{tarD}$ sequence could be differentially detected using PCR.

Figure 3B:
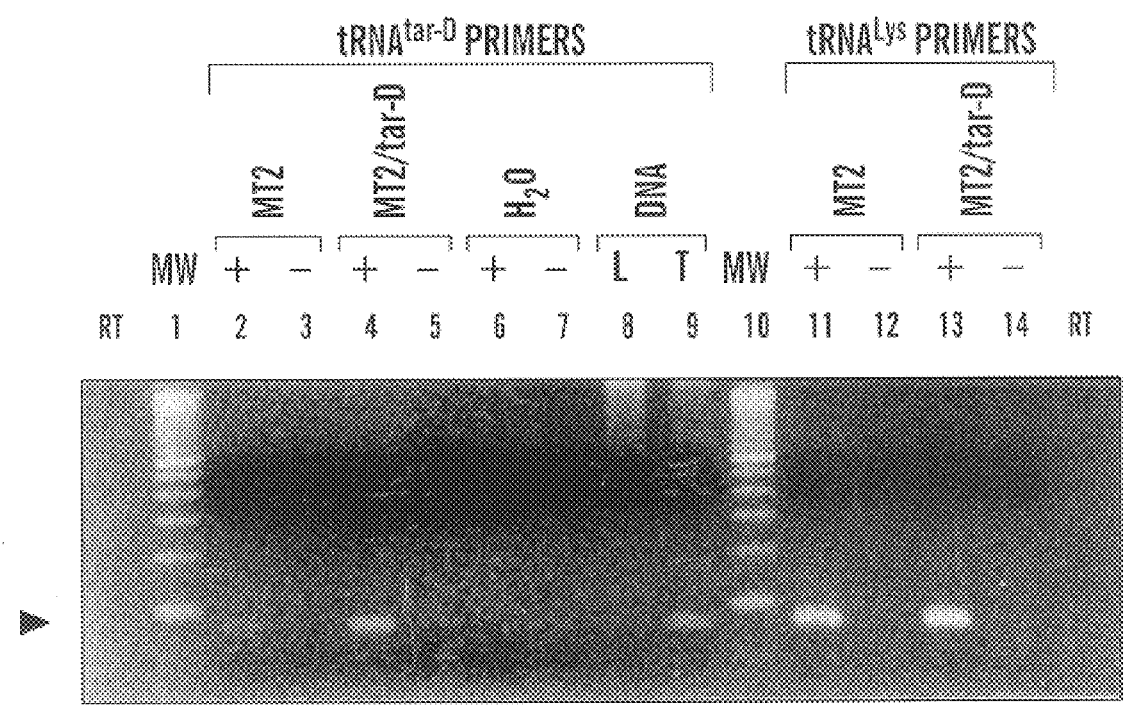
FIG. 3B is an analysis of pooled G418-resistant MT-2/TARD cells for tRNAtarD expression using RT-PCR. Cytoplasmic RNA was extracted as described in the Examples. Reverse transcription was performed by incubation of 2 μg of indicated RNA or H$_2$O in the presence ("+" lanes) or absence "−" lanes) of SuperScript II reverse transcriptase and a tRNA$^{Lys3}$- or tRNAtarD-specific primer as indicated. Synthesized cDNA was amplified by PCR, and products were analyzed in 2% agarose gels. 100 ng of DNA from MT-2 (lane 8) and MT-2/TARD (lane 9) cells were amplified as negative and positive controls, respectively.

Expression of mutant tRNA$^{tarD}$ in the cells was examined following transduction (FIG. 3B). Using selective RT-PCR, a band with the size of mutant tRNA$^{tarD}$ RNA was detected in MT-2/TARD cells (lane 4), but was not observed in parental MT-2 cells (lane 2). No band was detected in the MT-2/TARD cells when PCR was carried out in the absence of RT (lane 5), indicating that the target band obtained in the MT-2/TARD cells was derived from RNA, and not residual DNA contamination. In contrast, a characteristic band resulting from tRNA$^{Lys3}$ was detected with similar intensity in both parental MT-2 and MT-2/TARD cells, when the RNA samples were amplified with tRNA$^{Lys3}$ primers (FIG. 3B, lanes 11 and 13). Although less intense signals were detected compared to those of tRNA$^{Lys3}$, mutant tRNA$^{tarD}$ transcripts were readily detected in transduced MT-2/TARD cells. Northern blotting and hybridization with a radiolabeled tRNA$^{tarD}$ specific probe confirmed tRNA$^{tarD}$ expression.

Example 4
TCID$_{50}$ Assay for tRNA$^{tarD}$ Effects on HIV-1 Replication

Figure 4A:
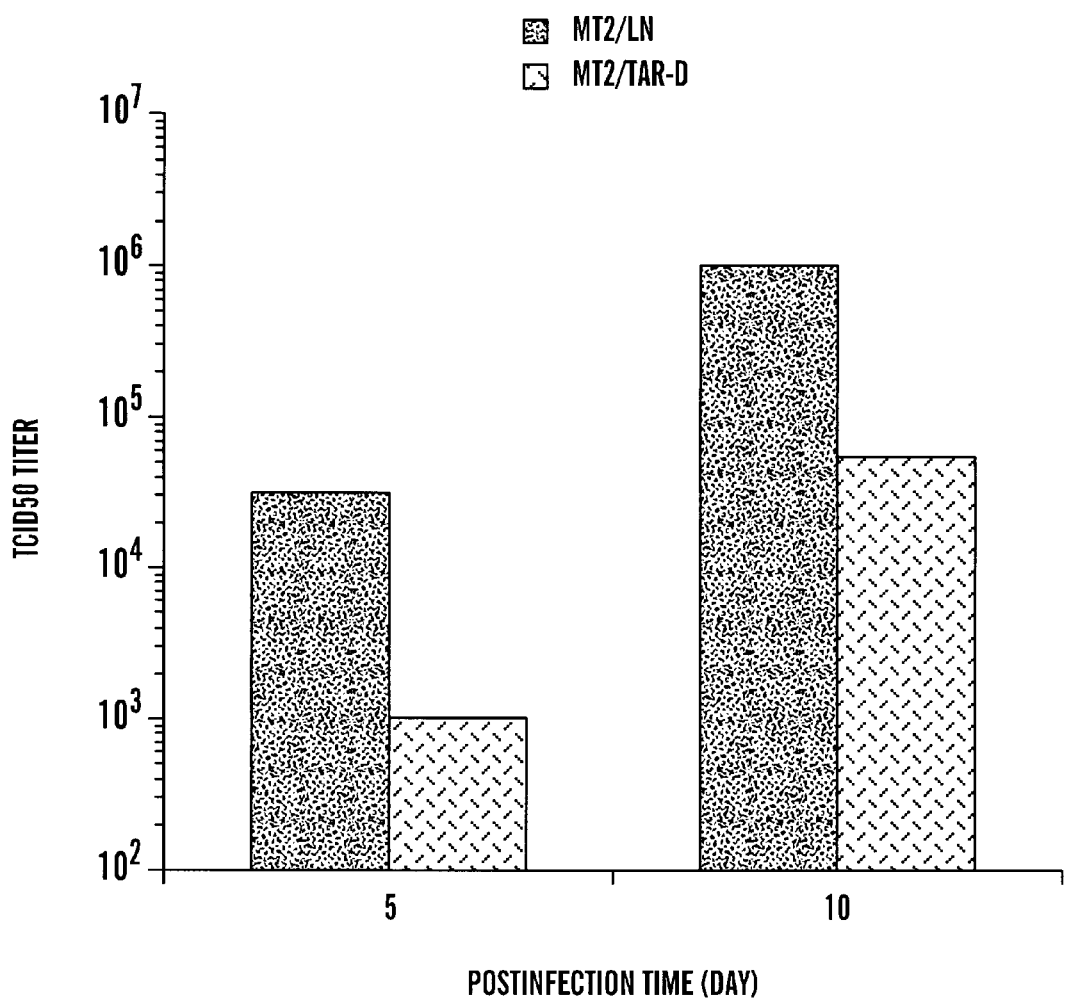
FIG. 4A is a comparison of TCID$_{50}$ titers of an HIV-IIIB stock using parental MT-2 and uncloned pooled MT-2/TARD cells.
Figure 4B:
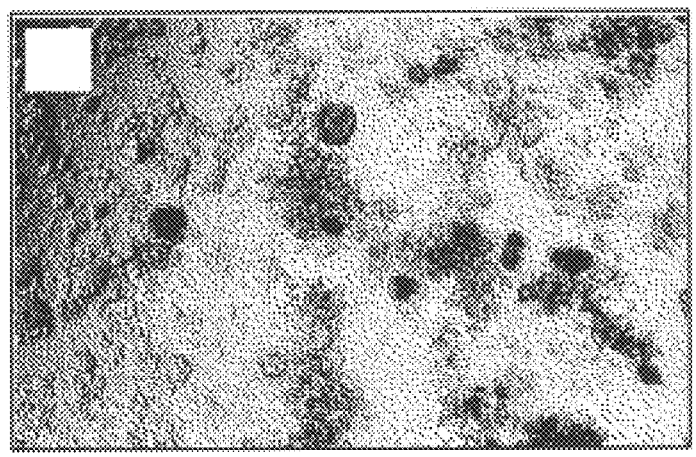
FIG. 4B shows phase contrast photomicrographs of syncytium formation induced by inoculation of HIV-IIIB (360 TCID$_{50}$/ml) in MT-2/TARD cells.
Figure 4C:
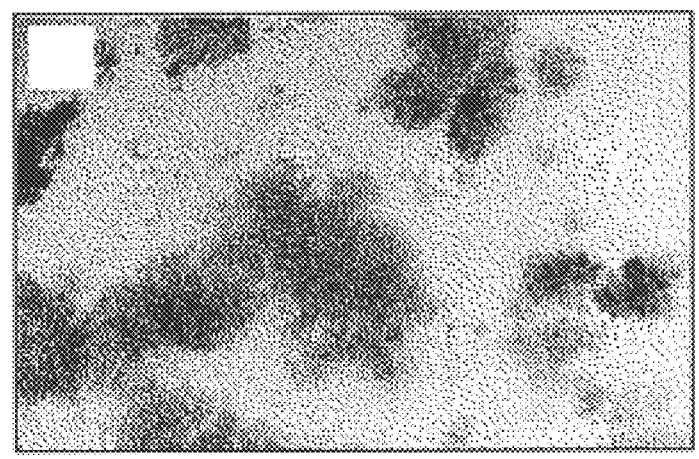
FIG. 4C depicts syncytium formation in control M-T2/LN cells inoculated with HIV-IIIB as in previous panel.

To examine the relative sensitivity of the transduced MT-2/TARD cells to HIV-1, an infectious stock of HIV-IIIB was simultaneously titered in both control MT-2/LN cells and pooled G418 resistant MT-2/TARD cells (FIG. 4). MT-2/TARD cells had a lower calculated TCID$_{50}$ (FIG. 4C) than control cells, MT-2/LN (FIG. 4C). As shown in FIG. 4, panel A, the TCID$_{50}$ titer obtained at day 5 p.i, was 10$^{4.5}$ in MT-2 cells as compared to 10$^{3.0}$ in MT-2/TARD cells. The relative estimated titers increased with time and reached 10$^{6.0}$ in parental MT-2 cells and 10$^{4.8}$ in the MT-2/TARD cells, respectively, at day 10 p.i. The estimated viral titers did not change significantly with extended incubation of up to 15 days. This assay was repeated several times with similar results. The estimated viral titer in pooled G418 resistant MT-2/TARD cells was reproducibly 1.0–1.2 log lower than that of control MT-2/LN cells, or MT-2/LN cells not expressing mutant tRNA$^{tarD}$. In addition, the frequency of syncytia formation in pooled G418-resistant MT-2/TARD cells was much lower (FIG. 4B) than that in parental MT-2 cells (FIG. 4C) when using an identical viral inoculum.

Figure 5A:
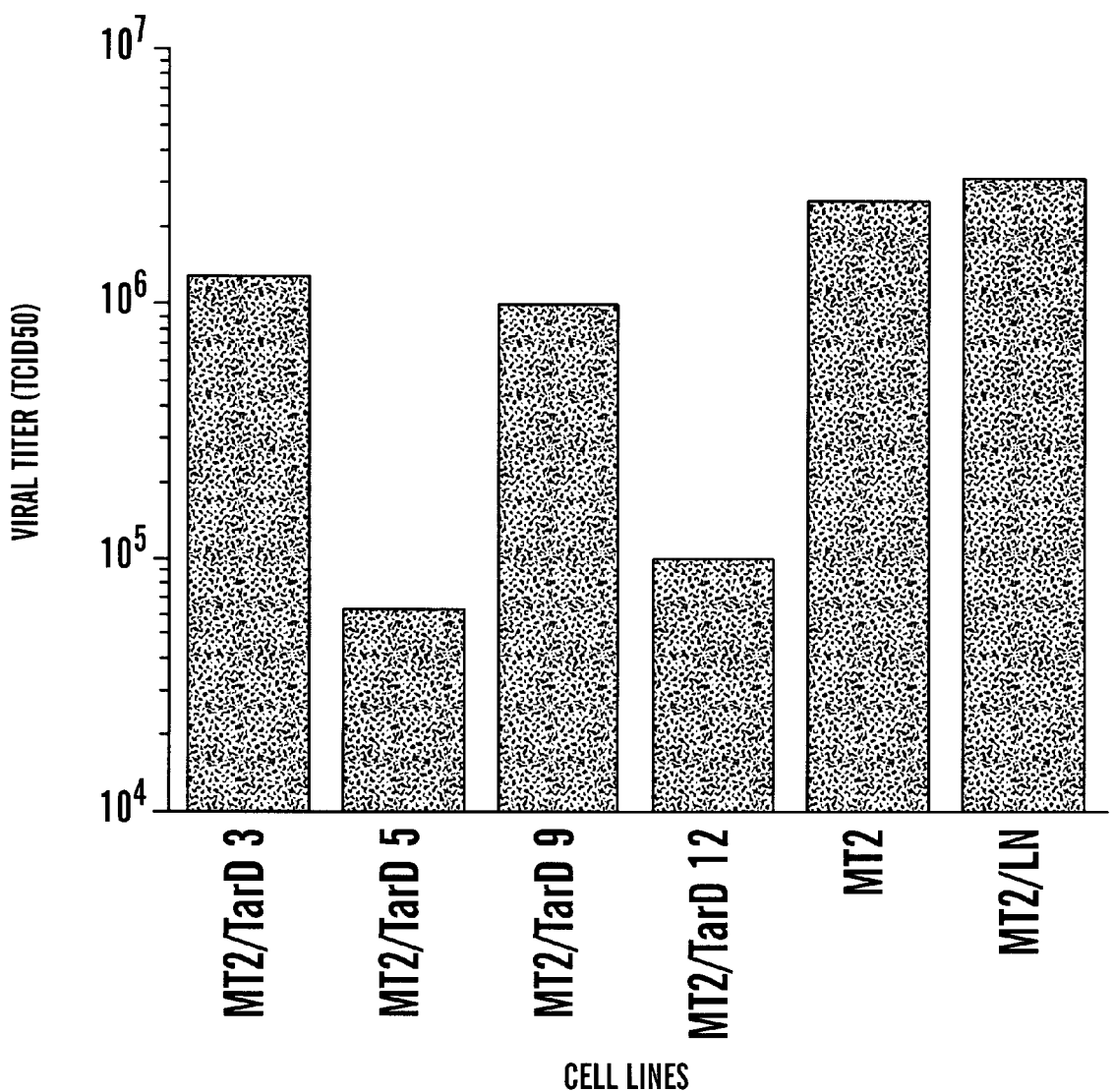
FIG. 5A is a comparison of TCID$_{50}$ titers determined in selected subclones of MT-2/TARD cells from a HIV-IIIB stock. The infected cultures were incubated at 37° C. and the viral titers were determined at postinfection day 14.

Multiple subclones were obtained from the pooled transduced MT-2/TARD cells by dilution cloning. The relative ability of these subclones to support HIV-1 replication by the TCID$_{50}$ assay was determined. Although relative titers varied among different subclones, all subclones tested showed decreased TCID$_{50}$ titers compared to control MT-2 or MT-2/LN cells. As shown in FIG. 5A, the TCID$_{50}$ titers measured for subclones No. 5 and No. 12 were $10^{4.8}$ and $10^{5.0}$, respectively. These two sub-clones were the most refractory to HIV-1 replication, showing a marked decrease (>1.5 log) in virus titers compared to control MT-2 cells ($10^{6.4}$) or MT-2/LN ($10^{6.5}$) Subclones No. 3 and 9, representing the least resistant clones, exhibited a lower but detectable drop (<0.3 log) in virus titers compared to control cells.

Figure 5B:
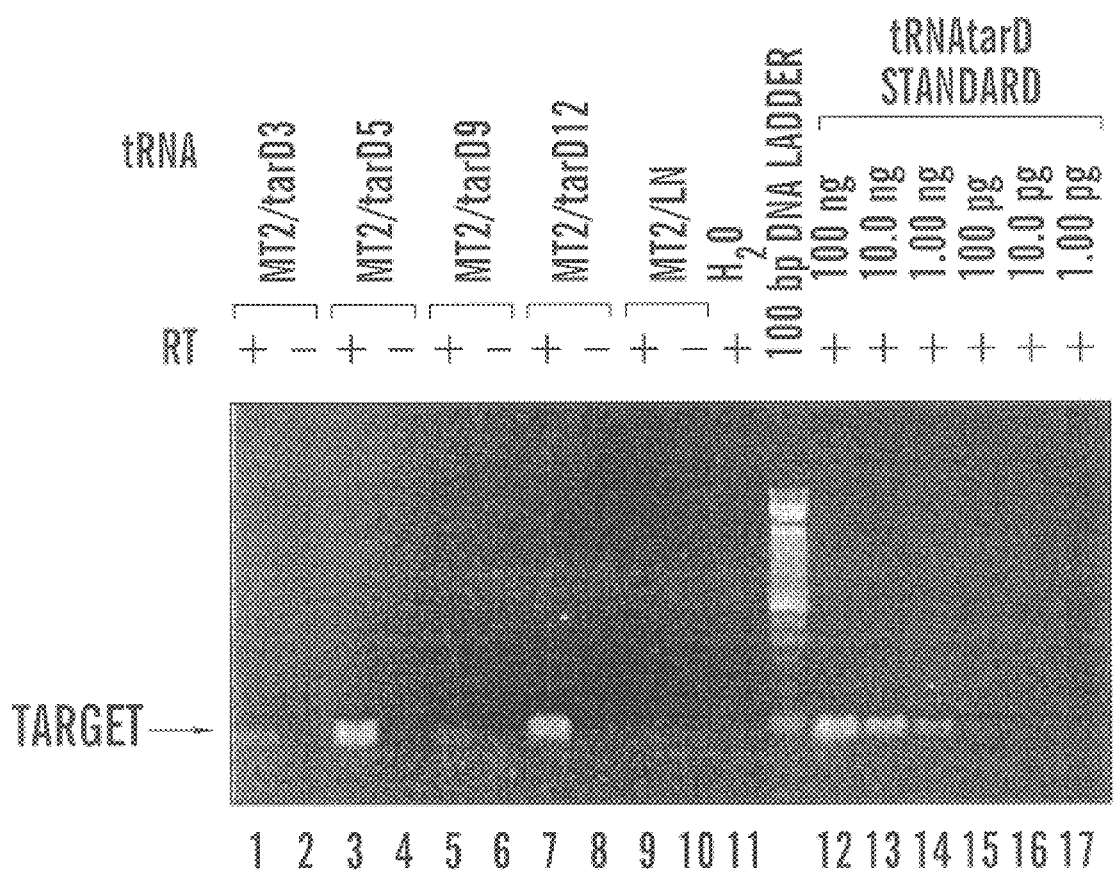
FIG. 5B is a comparison of tRNAtarD expression in selected MT-2/TARD subclones by RT-PCR. RT-PCR conditions used were the same as described in FIG. 3B. Primers, cellular tRNA sources, and controls are indicated above each lane.

Examination of the tRNA$^{tarD}$ expression in selected subclones No. 3, 5, 9 and 12 using RT-PCR indicated that the level of expression of the mutant tRNA$^{tarD}$ varied among these subclones. When the same amount (2 μg) of cellular RNAs were amplified by the tRNA$^{tarD}$ specific primers, the tRNA$^{tarD}$ signals observed for subclones No. 5 and 12 (lanes 3 and 7) were increased relative to those for subclones No. 3 and 9 (FIG. 5B, lanes 1 and 5). These results suggested that the level of tRNA$^{tarD}$ expression correlated with the efficiency of HIV-1 inhibition.

Example 5
Viral p24 Assay Following HIV-1 Challenge

Figure 6:
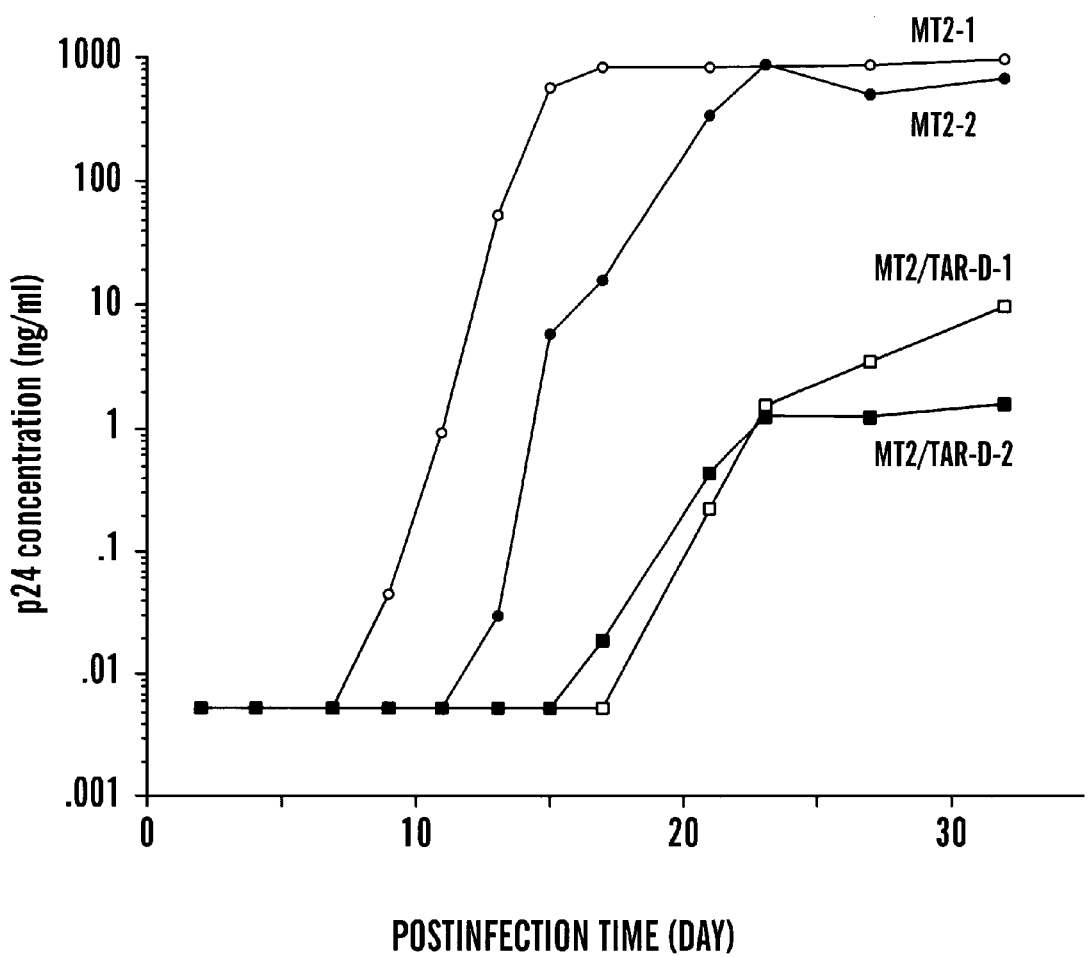
FIG. 6 is a comparison of HIV-IIIB replication as assayed by p24 production in MT-2/LN and MT-2/TARD (subclone 5). No. 1 and 2 represent duplicate infections.

To further assess the inhibitory effect of tRNA$^{tarD}$ on HIV-1 replication, subclone No. 5 was tested for its ability to support HIV-1 replication. Following HIV-1 infection, HIV-1 p24 viral antigen was initially detected on day 9 in the control MT-2/LN cultures, and reached a peak on day 17 (FIG. 6). In contrast, p24 antigen was not detected until day 17 in MT-2/TARD cells, demonstrating a delay of approximately 8 days in p24 production compared to control cells. Visible syncytia appeared in the control cultures at day 12 p.i. and involved most of the cells by day 17. In contrast, very few syncytia were observed even after 27 days p.i. in MT-2/TARD cells. Qualitatively similar results were also observed in CEM cells transduced with N2A-tarD relative to parental CEM cells (data not shown). These measurements demonstrated that tRNA$^{tarD}$ expression resulted in decreased HIV-1 infection as assayed by either p24 production or relative titer of the same HIV-1 stock.

Example 6
Analysis of tRNA$^{tarD}$ Incorporation into HIV-IIIB Virions

Figure 7:
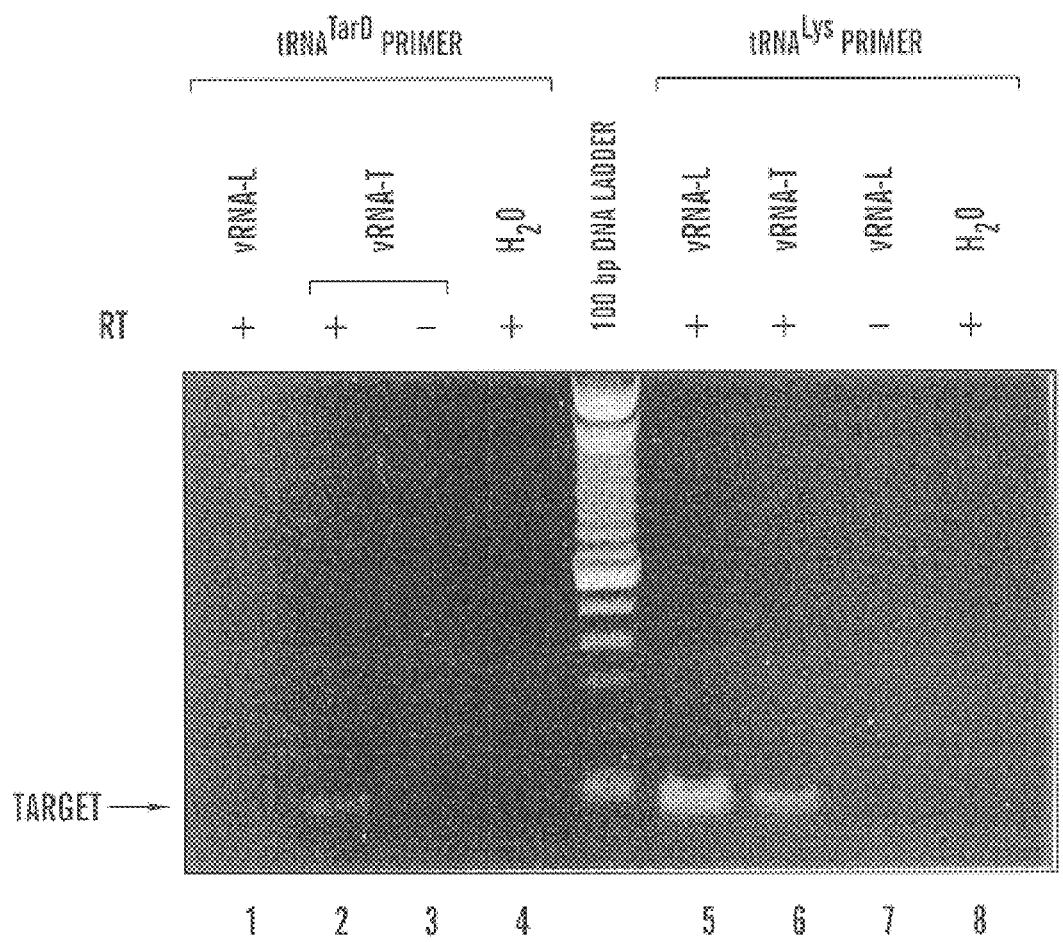
FIG. 7 shows the detection of incorporation of the mutant tRNAtarD into virions by RT-PCR. RT-PCR conditions are the same as described for cellular tRNA detection except that 0.2 μg of total viral RNA was employed per reaction. VRNA-L indicates viral RNA extracted from HIV-IIIB propagated in MT-2/LN cells. VRNA-T means that viral RNA was prepared from HIV-IIIB propagated in pooled G418-resistant MT-2/TARD cells. Viral RNA sources, primers, and controls are indicated above each lane.

To determine whether mutant tRNA$^{tarD}$ was incorporated into HIV-1 virions, total viral RNA from $10^9$ TCID$_{50}$ of infectious virus was extracted from HIV-IIIB virus propagated in MT-2/TARD cells, or from virus produced in MT-2/LN cells. The results of RT-PCR amplification of viral RNAs, designed to detect the tRNA$^{tarD}$ sequence, is shown in FIG. 7. When viral RNAs were probed with tRNA$^{tarD}$ specific primers, a product with the proper 75 bp size of tRNA$^{tarD}$ was detected in the viral RNA sample from HIV-IIIB propagated in MT-2/TARD cells (lane 2), but was not seen in viral RNA prepared from control virions (lane 1). No PCR products were observed in controls in which either viral RNA or RT was absent (lanes 3 and 4). However, PCR products were detected in both control and target viral RNAs when the tRNA$^{Lys3}$ specific primers were used (lanes 5 and 6). These results indicated that mutant tRNA was incorporated into HIV-IIIB prepared from MT-2/TARD cells.

Decreased viral replication could also have been caused by a change in the rate of cell division. Therefore, the rate of growth of MT-2 and MT-2/TARD cells was studied. Comparison of growth kinetics indicated that the growth rate of MT-2/TARD was indistinguishable from that observed in parental MT-2 cells and MT-2/LN cells. Flow cytometric analysis showed that CD4 expression in MT-2/TARD cells was equal to that in parental MT-2 or MT-2/LN cells. Therefore, differences in HIV-1 replication could not be attributed to changes in cell growth kinetics or CD4 density.

Example 7
Anti-sense Effect of tRNA$^{tarD}$ on Viral Replication

A previous report demonstrated that the TAR loop was a suitable target for inhibition of HIV-1 replication using anti-sense RNA (Chatterjee, S., et al., Science 258, 1485–1488 (1992), which is hereby incorporated by reference). It is possible that tRNA$^{tarD}$ inhibits HIV replication by binding to the TAR loop in viral mRNA, therefore, interfering with Tat-mediated transactivation. A second possibility is that binding of tRNA$^{tarD}$ to the TAR loop in viral mRNAs would prevent their efficient expression. These possibilities were tested by measuring basal and Tat-induced transcriptional activities of the IV-1 LTR in the presence or the absence of tRNA$^{tarD}$ (Table 2). MT-2 cells were stably transfected with the LN (MT-2/LN) or N2A-tarD (MT-2/tarD) vectors. These cells were then transiently co-transfected with a construct in which the chloramphenicol acetyl transferase (CAT) reporter gene was driven by the HIV-1 LTR, and with a Tat expression vector (pSV-Tat) or control plasmid. Basal LTR activity in the absence of Tat was about two-fold higher in MT-2 LN than in MT-2 tarD cells, while Tat transactivation efficiencies were 23.4-fold in MT-2 LN cells, and 21.6-fold in MT-2 tarD cells. The above experiments suggest that expression of tRNAtarD did not markedly influence in the ability of Tat to transactivate the LTR. In addition, a moderate inhibitory effect on LTR-directed transcription cannot be excluded. Since the expression of tarD can inhibit viral production by several orders of magnitude, the potential anti-sense effects exerted by tarD may account only in part for the overall virus inhibition we observed.

TABLE 2

| | Plasmids | | |
|---|---|---|---|
| Cell type | HIV-LTR-CAT | pSV-Tat | CAT activity (cpm) |
| MT2/LN | + | − | 4,807 |
| | + | − | 4,990 |
| | + | + | 118,024 |
| | + | + | 110,719 |
| MT2/TARD pool | + | − | 3,408 |
| | + | − | 1,679 |
| | + | + | 46,578 |
| | + | + | 63,253 |

Table 1. Mechanism of inhibition of viral replication by tRNAtarD. Potential anti-sense effect of tRNAtarD on viral gene expression. MT2/LN and MT2/tarD cells were transfected with the plasmids pHIVLTRCAT, pSV-Tat and control plasmid as indicated, and chloramphenicol acetyl transferase activity was measured 48 hours post-transfection. Tat transactivation efficiencies were calculated by dividing CAT activity with pSV-Tat by CAT activity obtained with control plasmid transfection.

Example 8
Evidence that tRNA$^{tarD}$ Alters Priming of DNA Synthesis tRNA$^{tarD}$ should interfere with normal initiation of DNA synthesis. Consequently, the ability of tRNA$^{tarD}$ to prime HIV-1 RT-directed reverse transcription from a segment of HIV-1 genomic RNA (RNA 1) was measured. The RNA 1 segment used includes sequences from the PBS to the 5' end of the viral RNA. Reactions were carried out in vitro using highly purified HIV-1 RT, and either the tRNA$^{tarD}$ or the tRNA$^{Lys3}$. Control reactions were also carried out using three DNA primers (FIG. 8A). Expected extension products of lengths 368, 237 and 200 from DNA primers 1, 2, and 3, respectively, were observed (FIG. 8B, lanes 4, 3 and 2). Extension of the control primers to correct lengths demonstrates that RNA 1 can serve as an effective template for DNA synthesis primed from a variety of locations. Extension of the tRNA primer at the PBS would be expected to yield a product 416 nucleotides in length, whereas priming at the TAR loop homology gito would generate a 243 nucleotide-long product. As expected, priming by tRNA$^{Lys3}$ produced a 416-nucleotide long product (FIG. 8B, lane 5). Priming by tRNA$^{tarD}$ also produced a 416-nucleotide long product (FIG. 8B, lane 5). Priming by tRNA$^{tarD}$ also produced a 416-nucleotide band, indicating that, despite the introduction of mutations in tRNA$^{tarD}$, the residual complementarity was sufficient to prime reverse transcription at the PBS (FIG. 8B, lane 6). A band is also visible at about position 243, consistent with extension of tRNA$^{tarD}$ from its intended binding site on the TAR stem-loop. However, the observed band could also have been caused by normal pausing of polymerization during synthesis of the 416 nucleotide product. One potential effect of the observed priming by tRNA$^{tarD}$ at the PBS would be to introduce foreign sequences into the PBS of viral progeny.

In order to improve the ability to see potential products of priming from the intended tRNA$^{tarD}$ binding site, synthesis was measured from a shorter viral RNA template containing the TAR loop sequences but not the PBS (RNA 2). A 243 nucleotide-long product was observed consistent with priming within the stem of the TAR hairpin (FIG. 8D, lane 2). No extension products were observed in control experiments containing either tRNA$^{Lys3}$ or DNA primer 1 plus RNA 2, since neither primer was expected to bind the template (FIG. 8D, lane 1 and FIG. 8C, lane 1). Products of expected lengths were observed using DNA primers 2 and 3 on RNA 2 (FIG. 8C, lanes 3 and 2). This result demonstrates that RT-directed priming can also occur from a site outside of the PBS. During infection, this would produce a short reverse transcript, likely to disrupt viral replication.

Mutations were introduced into tRNAlys-UUU (tRNA$^{Lys3}$) designed to alter PBS binding specificity, while maintaining conserved sequence in the so-called "A" and "B" boxes needed for polymerase III-directed transcription (Geiduschek, et al., *Ann. Rev. Biochem.* 57, 873–91 (1988), which is hereby incorporated by reference), and maintaining integrity of the anticodon region. Sequences were substituted in the acceptor stem, to make a 3' domain complementary to the conserved HIV-1 TAR region. To ensure efficient transcription of this mutated gene, flanking 5' sequences were included which may contain enhancers for polymerase III-directed transcription. Also included were 3' flanking sequences consisting of the stop signal for polymerase III, and nucleotides required for processing, derived from the most efficiently expressed of the three cellular tRNAlys-UUU loci (Roy, et al., *Nuc. Acids Res.* 10, 7313–7322 (1982); Doran, et al., *Gene* 65, 329–336 (1988), which are hereby incorporated by reference). The mutant TRNA was also designed to maintain essential features, in regions away from the 3' end, required for interaction with HIV-1 RT and NCp7 (Barat, et al., *Embo. J.* 8, 3279–85 (1989); Barat, C., et al., *J. Mol. Biol.* 231, 185–90 (1990), which are hereby incorporated by reference). Expression of mutant tRNAtarD in cultured T-cells did not alter cellular morphology, the rate of cell division, or CD4 antigen expression, suggesting it did not interfere with the function of the cellular tRNA$^{Lys3}$.

Mutant tRNAtarD expression results in decreased HIV-1 replication, as assayed by p24 levels, or by relative TCID$_{50}$ titer in the MT-2 and CEM T-cell lines. Analysis of multiple transduced subclones showed a correlation between levels of tRNAtarD expression and HIV-1 inhibition.

Although the exact mechanism by which mutant tRNA expression protects cells against HIV-1 challenge is not yet known, several possibilities exist. Several reports indicated that p66 of the HIV-1 RT p51/p66 heterodimer recognizes and binds to the tRNA$^{Lys3}$ anticodon region (Sarih-Cottin, et al., *J. Mol. Biol.* 226, 1–6 (1992); Kohlstaedt, et al., *Proc. Natl. Acad. Sci. USA* 89, 9652–9656 (1992); DeVico, et al., *J.Biol. Chem.* 266, 6774–6779 (1991); Rhim, et al., *J. Virol.* 65, 4555–64 (1991), which are hereby incorporated by reference) and may help unwind the acceptor stem (Kohlstaedt, et al., *Proc. Natl. Acad. Sci. USA* 89, 9652–9656 (1992), which is hereby incorporated by reference) in the presence of NCp7 protein (Barat, et al., *Nucleic Acids Res.* 19, 751–7 (1991), which is hereby incorporated by reference). Another report demonstrated that excess wild type tRNA$^{Lys3}$ primer inhibited the DNA polymerase activity of a recombinant HIV-1 RT, p66/p51 heterodimeric form (Bordier, et al., *Nucleic Acids Res.* 18, 429–36 (1990), which is hereby incorporated by reference). This effect was ascribed to the anticodon region of tRNA$^{Lys3}$ primer (Bordier, et al., *Nucleic Acids Res.* 18, 429–36 (1990), which is hereby incorporated by reference). As mutant tRNAtarD levels appear to be lower than endogenous tRNA$^{Lys3}$, direct competition is not likely to be the primary mechanism for inhibition of viral replication.

Although tRNAtarD can bind to RT, it was expected that it would not prime reverse transcription from the correct PBS since tRNAtarD lacks significant complementary sequences to the 5' region of the HIV-1 PBS (FIG. 9). However, results of priming assays carried out in vitro using purified HIV-1 RT demonstrate that the tRNAtarD can prime at either the PBS or the intended binding site in the TAR stem-loop. Significantly, the three 3'-most nucleotides in tRNAtarD (5'-CCA-3'), which are post-transcriptionally added to all tRNAs, are complementary to the corresponding nucleotides in the PBS. Alternatively, tRNAtarD-directed priming from the PBS would introduce a foreign sequence into the PBS which could interfere with the second strand transfer step of viral replication. In this step, the sequences copied into DNA from the modified region of tRNAtarD have to bind to sequences complementary to the normal PBS sequence to complete synthesis of the double stranded DNA intermediate of viral replication. Introduction of a foreign sequence into the PBS could have additional effects, such as lowering the efficiency of priming by normal tRNA$^{Lys3}$ in the altered virus. This could affect both replication in infected cells, and the ability of the virus to infect new cells. tRNAtarD-directed priming from the TAR sequence would make a viral minus strand DNA that is too short to complete synthesis. Aberrant cDNA synthesis could also lead to premature viral RNA template degradation by the RNase H activity of HIV-1 RT, in theory leading to production of integration-defective proviral DNA.

Inhibitory effects may be enhanced further by the selective packaging of this mutant tRNA into virions, since the PBS is not thought to be required for selective incorporation of $tRNA^{Lys3}$ (Rhim, et al., *J. Virol.* 65, 4555–64 (1991); Wakefield, et al., *J. Virol.* 68, 1605–1614 (1994), which are hereby incorporated by reference) and since incorporation into the virions is thought to be mediated by interaction of Pr160-pol precursor with the tRNA anticodon region (Mak, et al., *J. Virol.* 68, 2065–72 (1994), which is hereby incorporated by reference). The incorporation of mutant tRNA-tarD into virions was observed. Infectivity of virus particles produced in cells expressing mutant tRNAtarD is decreased compared to wild type virions, when normalized for p24 levels. Mutant tRNAs with homology to sequences other than the PBS may result in the production of defective virions.

Potential mutations leading to adaptation to growth in MT2/TARD cells include alterations in the PBS to acquire complementarity to TAR, mutations in TAR to reduce complementarity to mutant tRNAtarD, or mutations within RT to decrease affinity for mutant tRNA. In vitro results suggested that tRNAtarD was preferentially priming DNA synthesis at the PBS (FIG. 7). To ascertain whether the appearance of breakthrough viruses might be a result of mutations in the PBS, sequence analysis of eleven independent PCR clones showed absence of mutations in the PBS and adjacent areas. This result may have several explanations. First, mutations elsewhere in the genome (i.e., the TAR region, RT coding sequence) may allow viruses to escape the inhibition by tRNAtarD. It is also possible that the production of such mutations does not occur, and the high levels of p24 production in MT2/TARD cells at late time points is a result of virus amplification beyond the inhibitory capacity of tRNAtarD. In this case, one would conclude that the inhibition of viral replication by tRNAtarD is simply more effective at low virus titers (i.e., early in infection) than at high virus titers.

Adverse effects of $tRNA^{tarD}$ expression on human T-cell lines were not observed as assayed by morphologic examination, CD4+ expression or changes in growth kinetics. Although the alterations which were introduced will preclude interactions with cellular aminoacyl transferase, the safety of this approach remains to be established. Rare neurologic syndromes have been described in patients with mutations in mitochondrial $tRNA^{Lys3}$ (Goto, Y., et al., *Biochem. Biophys. Res. Commun.* 202, 1624–1630 (1994); Hammans, et al., *Brain* 116, 617–632 (1993); Silvestri, G., et al., *Am. J. Hum. Genet.* 51, 1213–7 (1992); which are hereby incorporated by reference). Whether hematopoietic or lymphoid survival will be negatively affected in vivo by introduction of tRNAtarD is not known. However, preliminary results in T-cell lines suggest that there is no apparent toxicity, and that tRNAtarD may be useful as an anti-HIV-1 therapeutic strategy.

A major inhibition of HIV-1 replication in cells expressing mutant tRNAtarD has been observed. This strategy may offer advantages relative to conventional anti-sense because of the specific interaction of HIV-RT with $tRNA^{Lys3}$ derivative molecules, and the apparent ability of modified tRNAs to interfere with reverse transcription. The use of $tRNA^{Lys3}$ mutants with altered primer binding specificity to target HIV-1 replication may represent a novel gene therapy approach for acquired immunodeficiency syndrome (AIDS).

Although preferred embodiments have been depicted and described in detail herein, it will be apparent to those skilled in the relevant art that various modifications, additions, substitutions, and the like can be made without departing from the spirit of the invention and these therefore are considered within the scope of the invention as defined in the claims which follow.

What is claimed:

1. A modified human tRNA$^{Lys3}$ molecule for inhibiting HIV-1 replication comprising:
a human tRNA$^{Lys3}$ molecule comprising an acceptor stem, a primer region, and a TΨC loop, wherein the human tRNA$^{Lys3}$ molecule comprises one or more mutations in the primer region or the TΨC loop, wherein the 5' segment of the acceptor stem is complementary to the 3' segment of the acceptor stem to maintain the secondary structure of the acceptor stem and the 5' segment of the TΨC loop stem is complementary to the 3' segment of the TΨC loop stem to maintain the secondary structure of the TΨC loop, and wherein the 3' terminal ACC-5' is added post-transcriptionally.

2. The modified tRNA$^{Lys3}$ molecule according to claim 1, wherein the 3' segment of the acceptor stem or the TΨC loop stem is complementary to a segment of the HIV-1 outside of the primer binding site.

3. The modified tRNA$^{Lys3}$ molecule according to claim 1, wherein the 3' segment of the acceptor stem or the TΨC loop stem has no complementarity to HIV-1.

4. The modified tRNA$^{Lys3}$ molecule according to claim 1, wherein the TΨC loop is mutated to decrease HIV replication.

5. The modified tRNA$^{Lys3}$ molecule according to claim 4, wherein the TΨC loop is mutated at a position selected from the group of modified tRNA bases consisting of position 58, position 55, and position 54.

6. The modified tRNA$^{Lys3}$ molecule according to claim 4, wherein the TΨC loop is mutated in a $^{50}$AGGGTmΨ$^{55}$ motif.

7. The modified tRNA$^{Lys3}$ molecule according to claim 1, where the 3' segment of the acceptor stem comprises a nucleic acid sequence as shown in SEQ ID NO: 1.

8. The modified tRNA$^{Lys3}$ molecule according to claim 1, wherein the 5' segment of the acceptor stem comprises a nucleic acid sequence 5'-UAGACC-3'.

9. A gene encoding the modified human tRNA$^{Lys3}$ molecule of claim 1.

10. The gene of claim 9, wherein the modified human tRNA$^{Lys3}$ molecule coding sequences are functionally linked to a promoter.

11. The gene of claim 10, wherein the promoter promotes expression of the gene in human cells.

12. The gene of claim 11, wherein the promoter is a pol III promoter.

13. An expression vector carrying the gene of claim 11.

14. The expression vector according to claim 13, wherein the vector is a viral vector or an oligonucleotide.

15. The expression vector according to claim 14, wherein the viral vector is a retroviral vector or an adeno-associated virus vector.

16. A host cell transduced with the gene of claim 11.

17. The host cell of claim 16, wherein the host cell is a T-cell.

* * * * *

SEQUENCE LISTING

```
<160> NUMBER OF SEQ ID NOS: 20

<210> SEQ ID NO 1
<211> LENGTH: 10
<212> TYPE: RNA
<213> ORGANISM: Artificial Sequence
<220> FEATURE:
<223> OTHER INFORMATION: Description of Artificial Sequence:  tRNA
      fragment

<400> SEQUENCE: 1
ggucuaacca                                                           10

<210> SEQ ID NO 2
<211> LENGTH: 76
<212> TYPE: RNA
<213> ORGANISM: Artificial Sequence
<220> FEATURE:
<223> OTHER INFORMATION: Description of Artificial Sequence:  tRNA(tarD)

<400> SEQUENCE: 2
uagaccauag cucagucggu agagcaucag acuuuuaauc ugagggucca ggguucaagu      60
cccugugguc uaacca                                                    76
```

```
<210> SEQ ID NO 3
<211> LENGTH: 87
<212> TYPE: DNA
<213> ORGANISM: Artificial Sequence
<220> FEATURE:
<223> OTHER INFORMATION: Description of Artificial Sequence: primer

<400> SEQUENCE: 3
aattgctgca gtaatacgac tcactatagc ccggatagct cagtcggtag agcatcagac      60
ttttaatctg agggtccagg gttcaag                                          87

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 4
ctaagctgca gatgcatggc gcccgaacag ggacttgaac cctggaccct                 50

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 5
gtaatacgac tcactata                                                    18

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 6
ctaagctgca gatgcatggt tagaccacag ggacttgaac cctggaccct                 50

<210> SEQ ID NO 7
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 7
aattgctgca gtaatacgac tcactatata gaccatagct cagtcggtag agca            54

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 8
ctaagctgca gatgcatggt tagaccacag ggacttgaac cctggaccct                 50

<210> SEQ ID NO 9
<211> LENGTH: 36
<212> TYPE: DNA
<213> ORGANISM: Artificial Sequence
<220> FEATURE:
```

```
<223> OTHER INFORMATION: Description of Artificial Sequence:  primer

<400> SEQUENCE: 9
tcgccgagat aagcttcagc ctctactatg gtacag                              36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:  primer

<400> SEQUENCE: 10
ataatagcac aagctttatt accctccacc gtcgtt                              36

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence:  primer

<400> SEQUENCE: 11
gtaaagctct cgtgaagata gaccatagct cagtcggtag agc                      43

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence:  primer

<400> SEQUENCE: 12
ccaaaagcaa agacatgccg cttagaccac agggacttga accctggac                49

<210> SEQ ID NO 13
<211> LENGTH: 49
<212> TYPE: DNA
<213> ORGANISM: Artificial Sequence
<220> FEATURE:
<223> OTHER INFORMATION: Description of Artificial Sequence:  primer

<400> SEQUENCE: 13
gtccagggtt caagtccctg tggtctaagc ggcatgtctt tgcttttgg                49

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:  primer

<400> SEQUENCE: 14
ataatagcac aagctttatt accctccacc gtcgtt                              36

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:  primer

<400> SEQUENCE: 15
tagaccatag ctcagtcggt                                                20
```

```
<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 16
tggttagacc acagggactt                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 17
gcccggatag ctcagtcggt                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 18
tggcgcccga acagggactt                                              20

<210> SEQ ID NO 19
<211> LENGTH: 76
<212> TYPE: RNA
<213> ORGANISM: Homo sapiens

<400> SEQUENCE: 19
gcccggauag cucagucggu agagcaucag acuuuuaauc ugagggucca ggguucaagu   60
cccuguucgg gcgcca                                                  76

<210> SEQ ID NO 20
<211> LENGTH: 76
<212> TYPE: RNA
<213> ORGANISM: Artificial Sequence
<220> FEATURE:
<223> OTHER INFORMATION: Description of Artificial Sequence: tRNA(tar)

<400> SEQUENCE: 20
gcccggauag cucagucggu agagcaucag acuuuuaauc ugagggucca ggguucaagu   60
cccugugguc uaacca                                                  76
```